(12) United States Patent
Vorst et al.

(10) Patent No.: US 8,063,374 B2
(45) Date of Patent: Nov. 22, 2011

(54) SYSTEMS AND METHODS FOR DETERMINING RECYCLED THERMOPLASTIC CONTENT

(75) Inventors: Keith Vorst, San Luis Obispo, CA (US); Greg Curtzwiler, San Luis Obispo, CA (US); Jeffrey Danes, San Luis Obispo, CA (US); Phil Costanzo, San Luis Obispo, CA (US)

(73) Assignee: California Polytechnic Corporation, San Luis Obispo, CA (US)

( * ) Notice: Subject to any disclaimer, the term of this patent is extended or adjusted under 35 U.S.C. 154(b) by 191 days.

(21) Appl. No.: 12/564,902

(22) Filed: Sep. 22, 2009

(65) Prior Publication Data
US 2011/0068262 A1    Mar. 24, 2011

(51) Int. Cl.
*G01J 5/02*         (2006.01)
(52) U.S. Cl. ...... 250/339.08; 209/3.1; 702/22; 707/102; 356/51
(58) Field of Classification Search ............ 250/339.08; 209/3.1; 702/22; 707/102; 356/51
See application file for complete search history.

(56) References Cited

U.S. PATENT DOCUMENTS

| | | | |
|---|---|---|---|
| 5,417,904 A * | 5/1995 | Razi et al. | 264/129 |
| 5,688,693 A * | 11/1997 | Fine et al. | 436/43 |
| 5,859,071 A * | 1/1999 | Young et al. | 521/40.5 |
| 6,509,537 B1 * | 1/2003 | Krieg et al. | 209/579 |
| 6,533,124 B1 * | 3/2003 | Tacito et al. | 209/3.1 |
| 6,663,929 B1 * | 12/2003 | Tabota et al. | 428/35.7 |
| 6,869,687 B2 * | 3/2005 | Tadokoro et al. | 428/522 |
| 7,043,326 B2 * | 5/2006 | Neubauer et al. | 700/117 |
| 7,433,761 B2 * | 10/2008 | Battiste | 700/269 |
| 7,884,140 B2 * | 2/2011 | Riise et al. | 521/40 |
| 2003/0003297 A1 * | 1/2003 | Tadokoro et al. | 428/343 |
| 2004/0133364 A1 * | 7/2004 | Marrow et al. | 702/30 |
| 2005/0090567 A1 * | 4/2005 | Koike et al. | 521/40 |
| 2005/0179153 A1 * | 8/2005 | Riise et al. | 264/40.1 |
| 2006/0017914 A1 * | 1/2006 | Riess et al. | 356/51 |
| 2006/0148914 A1 * | 7/2006 | Connor et al. | 521/48 |
| 2008/0015720 A1 * | 1/2008 | Oyasato et al. | 700/97 |
| 2008/0301178 A1 * | 12/2008 | Venkataraman et al. | 707/102 |
| 2009/0119027 A1 * | 5/2009 | Venkataraman et al. | 702/27 |
| 2009/0227825 A1 * | 9/2009 | Briggs | 585/822 |
| 2010/0007047 A1 * | 1/2010 | Lau | 264/239 |
| 2011/0068262 A1 * | 3/2011 | Vorst et al. | 250/282 |

\* cited by examiner

*Primary Examiner* — David Porta
*Assistant Examiner* — Hugh H Maupin
(74) *Attorney, Agent, or Firm* — Martine Penilla Group, LLP

(57) ABSTRACT

A system and method of identifying a reference standard library for thermoplastic content includes preparing a plurality of samples of each one of a plurality of known ratios of virgin thermoplastic/recycled thermoplastic, analyzing each of the plurality of samples of each one of the plurality of known ratios of virgin thermoplastic/recycled thermoplastic with at least one of a group of analyses consisting of: a differential scanning calorimetry analysis; a physical thickness analysis; an ultraviolet-visible spectroscopy analysis; an attenuated total reflectance Fourier transform infrared spectroscopy analysis; a mechanical analysis; or a plasma atomic emission spectroscopic analysis. The method is also comprised of selecting a contaminant, identifying a first plurality of indicators output from the at least one of the group of analyses, identifying a second plurality of indicators from the first plurality of indicators, the second plurality of indicators being independent of the selected contaminant and optimizing the second plurality of indicators to identify a third plurality of indicators, the third plurality of indicators being quantitatively different of the selected contaminant wherein each one of the third plurality of indicators has at least one corresponding value for each one of the plurality of known ratios of virgin thermoplastic/recycled thermoplastic. Systems and methods for determining content of recycled thermoplastic in a thermoplastic sample are also disclosed.

10 Claims, 14 Drawing Sheets

SYSTEMS AND METHODS FOR DETERMINING RECYCLED THERMOPLASTIC CONTENT

The present invention relates generally to systems and methods for analyzing plastic materials and more particularly, to systems and methods for determining post consumer (i.e. recycled) content in a thermoplastic sample.

Many goods and services are marketed proclaiming percentages of post consumer (i.e., recycled) content in their products and/or product packaging. Reusing post consumer products and packaging materials are an important method of conserving natural resources, energy and reducing bulk in landfills.

Further, many plastic type materials do not decompose naturally for very many years, if at all. Further still, many such plastic type materials breakdown into toxic materials as part of their decomposition process. As a result, recycling such plastic materials are important steps toward reducing the impact of these materials on our environment.

Manufacturers have begun to make broad marketing claims regarding percentages of post consumer material content in their products and product packaging as consumers are becoming more and more aware of the impacts of plastic-type materials on the environment. Unfortunately, for many of these plastic materials, there is no standard, reliable system, method of determining actual contents of a claimed reused or recycled thermoplastic material in a given thermoplastic sample (e.g., a product or a product packaging). As a result, recent testing has shown many of the manufacturers' marketing claims of regarding percentages of post consumer material content are less than accurate and some may say specifically misleading to the consumer.

In view of the foregoing, there is a need for standard, reliable systems and methods of determining actual contents of a claimed reused or recycled thermoplastic material in a given thermoplastic sample.

SUMMARY

Broadly speaking, the present invention fills these needs by providing systems and methods of determining actual contents of a claimed reused or recycled thermoplastic material in a given thermoplastic sample. It should be appreciated that the present invention can be implemented in numerous ways, including as a process, an apparatus, a system, computer readable media, or a device. Several inventive embodiments of the present invention are described below.

One embodiment provides a method of identifying a reference standard library for thermoplastic content includes preparing a plurality of samples of each one of a plurality of known ratios of virgin thermoplastic/recycled thermoplastic, analyzing each of the plurality of samples of each one of the plurality of known ratios of virgin thermoplastic/recycled thermoplastic with at least one of a group of analyses consisting of: a differential scanning calorimetry analysis; a physical thickness analysis; an ultraviolet-visible spectroscopy analysis; an attenuated total reflectance Fourier transform infrared spectroscopy analysis; a mechanical analysis; or a plasma atomic emission spectroscopic analysis. The method is also comprised of selecting a contaminant, identifying a first plurality of indicators output from the at least one of the group of analyses, identifying a second plurality of indicators from the first plurality of indicators, the second plurality of indicators being independent of the selected contaminant and optimizing the second plurality of indicators to identify a third plurality of indicators, the third plurality of indicators being quantitatively different of the selected contaminant wherein each one of the third plurality of indicators has at least one corresponding value for each one of the plurality of known ratios of virgin thermoplastic/recycled thermoplastic.

The thermoplastic can be a polyethylene terephthalate (PET), a polyethylene, a polypropylene, a polystyrene, a poly methyl methacrylate, a polycarbonate, an addition polymer thermoplastic or a condensation polymer thermoplastic.

Analyzing each of the plurality of samples of each one of the plurality of known ratios of virgin thermoplastic/recycled thermoplastic can include analyzing each of the plurality of samples of each one of the plurality of known ratios of virgin thermoplastic/recycled thermoplastic with at least two of the group of analyses.

Another embodiment provides a method for determining content of recycled thermoplastic in a thermoplastic sample including: identifying a reference standard library for thermoplastic content including a plurality of indicators being quantitatively different of the selected contaminant, preparing a plurality of test samples of an known ratio of virgin thermoplastic/recycled thermoplastic for analysis, analyzing each one of the plurality of test samples of the unknown ratio of virgin thermoplastic/recycled thermoplastic with at least one of a group of analyses consisting of: a differential scanning calorimetry analysis, a physical thickness analysis, an ultraviolet-visible spectroscopy analysis, an attenuated total reflectance Fourier transform infrared spectroscopy analysis, a mechanical analysis or a plasma atomic emission spectroscopic analysis, wherein analyzing each one of the plurality of test samples of the unknown ratio of virgin thermoplastic/ recycled thermoplastic includes identifying a corresponding value for each one of the plurality of indicators quantitatively different of the selected contaminant for the unknown ratio of virgin thermoplastic/recycled thermoplastic, identifying a percentage of virgin thermoplastic and recycled thermoplastic includes comparing the corresponding value for each one of the plurality of indicators quantitatively different of the selected contaminant for the unknown ratio of virgin thermoplastic/recycled thermoplastic to the reference standard library.

Yet another embodiment provides a testing system for identifying a reference standard library for thermoplastic content comprising: a system for preparing a plurality of samples of each one of a plurality of known ratios of virgin thermoplastic/recycled thermoplastic, an analysis system for analyzing each of the plurality of samples of each one of the plurality of known ratios of virgin thermoplastic/recycled thermoplastic with at least one of a group of analyses consisting of: a differential scanning calorimetry analysis; a physical thickness analysis; an ultraviolet-visible spectroscopy analysis; an attenuated total reflectance Fourier transform infrared spectroscopy analysis; a mechanical analysis; or a plasma atomic emission spectroscopic analysis; selecting a contaminant; a first identifier for identifying a first plurality of indicators output from the at least one of the group of analyses; a second identifier for identifying a second plurality of indicators from the first plurality of indicators, the second plurality of indicators being independent of the selected contaminant; and an optimizer for optimizing the second plurality of indicators to identify a third plurality of indicators, the third plurality of indicators being quantitatively different of the selected contaminant wherein each one of the third plurality of indicators has at least one corresponding value for each one of the plurality of known ratios of virgin thermoplastic/recycled thermoplastic.

Yet another embodiment provides a testing system for determining content of recycled thermoplastic in a thermoplastic sample comprising: an identifier for identifying a reference standard library for thermoplastic content including a plurality of indicators being quantitatively different of the selected contaminant; a system for preparing a plurality of test samples of an known ratio of virgin thermoplastic/recycled thermoplastic for analysis; an analyzer for analyzing each one of the plurality of test samples of the unknown ratio of virgin thermoplastic/recycled thermoplastic with at least one of a group of analyses consisting of: a differential scanning calorimetry analysis; a physical thickness analysis; an ultraviolet-visible spectroscopy analysis; an attenuated total reflectance Fourier transform infrared spectroscopy analysis; a mechanical analysis; or a plasma atomic emission spectroscopic analysis; wherein analyzing each one of the plurality of test samples of the unknown ratio of virgin thermoplastic/recycled thermoplastic includes identifying a corresponding value for each one of the plurality of indicators quantitatively different of the selected contaminant for the unknown ratio of virgin thermoplastic/recycled thermoplastic and an identifier for identifying a percentage of virgin thermoplastic and recycled thermoplastic includes comparing the corresponding value for each one of the plurality of indicators quantitatively different of the selected contaminant for the unknown ratio of virgin thermoplastic/recycled thermoplastic to the reference standard library.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings.

DETAILED DESCRIPTION

Figure 1:
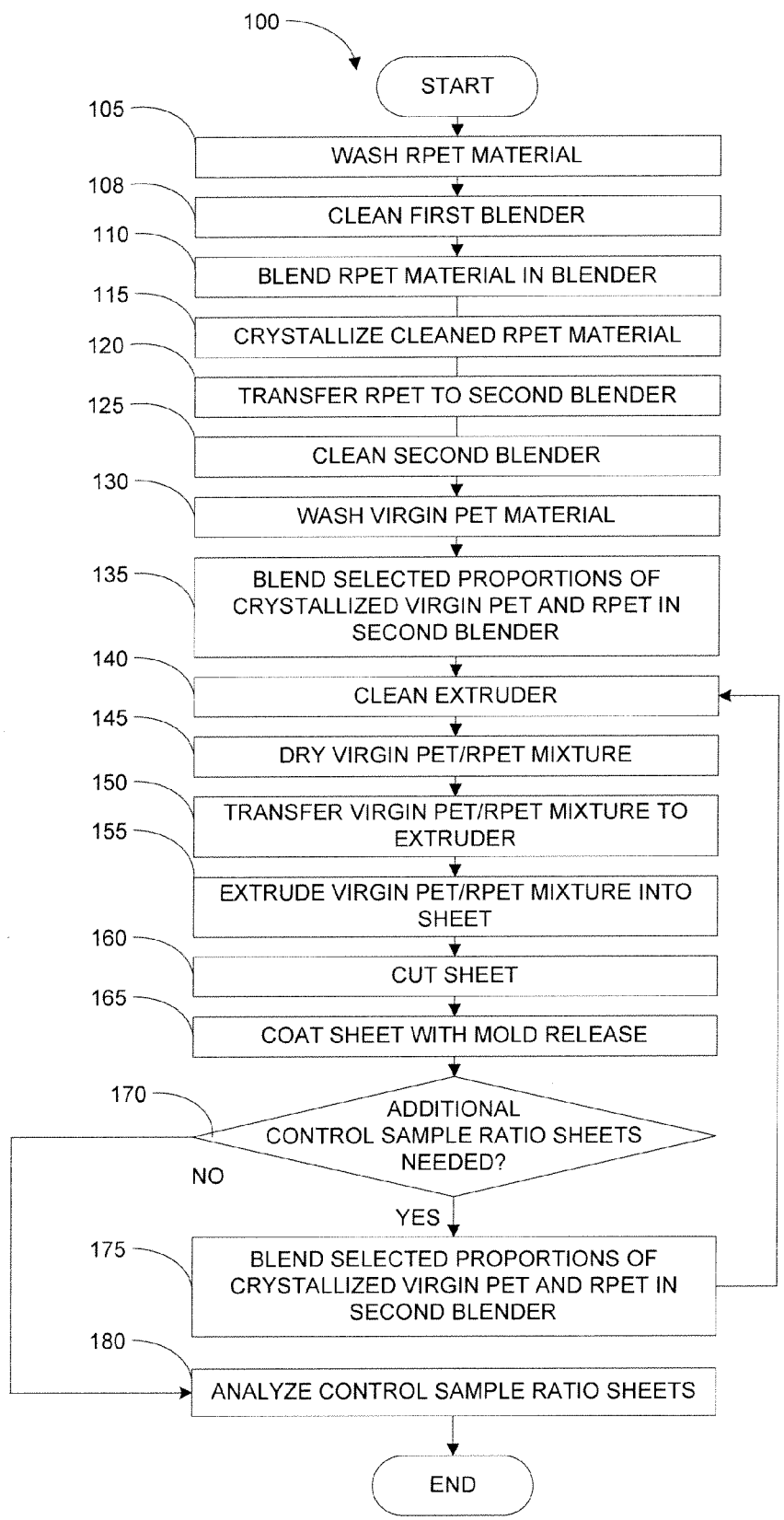
FIG. 1 is a flowchart of the method operations for producing the virgin PET/RPET control samples, in accordance with embodiments of the described invention.

Several exemplary embodiments for systems and methods of determining actual contents of a claimed reused or recycled thermoplastic material in a given thermoplastic sample will now be described. It will be apparent to those skilled in the art that the present invention may be practiced without some or all of the specific details set forth herein.

Identifying a Reference Standard Library

Standard, reliable systems and methods of determining actual contents of a claimed reused or recycled thermoplastic material in a given thermoplastic sample is a multi-step process. Initially, a reference standard library of content standards is identified. The reference standard library of content standards is identified by analyzing several control samples of the selected thermoplastic material. The control samples have known ratios of virgin material and recycled materials. Analyzing the control samples evaluates several physical and chemical properties of each control sample. Multiple samples of each control sample can be evaluated to provide more statistically accurate results.

Analyzing control samples yields corresponding reference values for each analysis, for each control sample having a known content ratio. Linear regression and Logit are applied to the resulting data from the control sample analyses to identify a reference standard library of characteristics for each known content ratio.

Unknown content ratio thermoplastic samples are evaluated using one or more of the same analytical procedures to evaluate the physical and chemical properties of each unknown sample. The analysis results of the unknown content sample(s) can be compared against the reference values in the reference standard library for one or more of the corresponding analyses. More analyses provide a more accurate determination of the properties of the unknown sample. Thus, a corresponding range of content for the unknown sample can be accurately determined.

While this may seem straight forward, the analytical process is rigorous, time consuming and expensive. Further, the baseline reference standard library has never before been complied and calculated.

These factors and others have caused most researchers to avoid such analysis. However, as the marketing claims become more widespread this lack of verification is raising the consciousness of this issue with the consumers and regulatory agencies. As a result, the consumers and some regulatory agencies are now seeking systems and methods to verify the marketing claims so as to protect consumers from being misled.

One such thermoplastic material is polyethylene terephthalate (PET). The following methods focus on PET as an exemplary material but it should be understood the methods and systems described herein could be applied to any type of thermoplastic material including, for example: polyethylene, polypropylene, polystyrene, poly methyl methacrylate, polycarbonate, plus other addition polymer thermoplastics and condensation polymer thermoplastics.

The amount of post-consumer PET (RPET) can be determined in PET sheets and PET thermoformed packaging (e.g., clamshells, blisterpacks, etc.) by utilizing the methodology described herein. The methodology includes the measurement of various chemical and physical properties of the unknown sample. The various chemical and physical properties of the unknown sample can be compared to a corresponding reference standard library to determine the post-consumer content. The methodology utilizes minimal equipment and consumables and requires minimal sample preparation time.

Production of Control Samples

Control samples use a known mixture of virgin PET and post consumer (i.e., recycled) PET (RPET). The process to combine the known quantities is repeated for each sample so that substantially consistent results can be obtained. The RPET may be obtained from a recycling source such as Eco 2 Plastics of Riverbank, Calif. FIG. 1 is a flowchart of the method operations 100 for producing the virgin PET/RPET control samples, in accordance with embodiments of the described invention. The operations illustrated herein are by way of example, as it should be understood that some operations may have sub-operations and in other instances, certain operations described herein may not be included in the illustrated operations. With this in mind, the method and operations 100 will now be described.

In an operation 105, a quantity of the RPET is washed to remove undesirable contaminants. Washing can include multiple sub steps such as washing with solvents, detergents, rinse agents and drying as are well known in the art.

In an optional, as may be required operation 108, a first blender is cleaned by cleaning with a suitable cleaning process or by purging if necessary. The first blender is purged to substantially remove any contaminants in the first blender.

In an optional operation 110, the washed RPET is transferred to the first blender (e.g., an AEC Whitlock (of Wooddale, Ill.) OS series blender or equivalent) and blended therein. The first blender reduces the RPET material to a substantially uniform size flake. Other devices and processes other than blenders could be used to provide a substantially uniform flake size and a substantially homogenized mixture. A typical PET flake size is between about 0.4 and about 8 mm in diameter.

In another optional operation 115, the blended RPET is transferred from the first blender to a crystallizer (e.g., such as is available from Con Air of Franklin, Pa., crystallizer model CG770 or equivalent). The RPET is crystallized in the crystallizer for about 45 minutes with an air temperature of 155° C. The crystallizer substantially crystallizes (e.g., aligns) the polymer chains in the RPET material to provide a substantially homogeneous density of the RPET. Depending on the source of the RPET material it may be produce from the source with sufficiently uniform flake size and crystallized form. The exemplary parameters described above are specifically for PET for the present specific process and would be changed to correspond with a different thermoplastic.

In an operation 120, the washed, blended, crystallized RPET is transferred to a second blender. In an operation 125, the second blender is purged to substantially remove contaminates from the second blender. The second blender can be purged by passing a sufficient quantity (e.g. about 2 to about 10 internal volumes of the second blender) of a purging material through the second blender. The washed, blended, crystallized RPET can be used as a purging material but other suitable purging materials can be used. It should be understood that the second blender could be the first blender as long as the first blender is sufficiently purged. The second blender is purged to substantially remove any contaminants in the second blender.

In an optional operation 130, a quantity of virgin PET is washed in substantially similar fashion to that of the RPET as described in operation 105 above. The virgin PET may be obtained from a reputable manufacturer such as Eastman in Columbia, S.C., model 992RP/BOL 252965, or equivalent. The virgin PET will have substantially similar crystalline form as the RPET described in operation 115 above. An optional subprocess may be required to sufficiently crystallize the virgin PET to the same density as the RPET although typically the RPET crystallization process in operation 115 above will have a known, as received, virgin PET crystallization and density as the desired RPET crystallization and density.

In an operation 135, a known amount of virgin PET is blended with the crystallized REPT in the second blender to obtain a selected control sample ratio of virgin PET to RPET. Several blends can be formed in batches with each batch having a different control sample ratio. The control sample ratios can be 0%/100% (100% RPET), 10%/90%, 20%/80%, 30%/70%, 40%/60%, 50%/50%, 60%/40%, 70%/30%, 80%/20%, 90%/10% and 100%/0% (100% virgin PET).

It should be understood that more or fewer control sample ratios could also be used. For example control sample ratios of 0%/100% (100% RPET), 20%/80%, 40%/60%, 60%/40%, 80%/20% and 100%/0% (100% virgin PET) could be used. It should be understood that 5%, or less (e.g., between about 1 and about 4%) control sample ratios steps could also be used. Similarly, combinations of 5%, 10%, and 20% control sample ratios steps could also be used. By way of example: 0%/100% (100% RPET), 2%/98%, 5%/95%, 7%/93%, 10%/90%, 12%/88%, 15%/85%, 17%/83%, 20%/80% (20% RPET and 80% virgin PET)

In an operation 140, the extruder is purged. The extruder can be purged for a desired time interval (e.g., between about 2 and about 20 minutes at a selected flow rate) or by a volume (e.g., between about 2 and about 10 internal volumes of the extruder apparatus) or any other suitable purging method. The extruder is purged to substantially remove any contaminants in the extruder. Extruder contaminants can include residual PET/RPET blends of the incorrect composition or other contaminants. The RPET blended in the second blender can be used to purge the extruder. Alternatively, the virgin PET or a mixture of the virgin PET and the RPET can be used to purge the extruder. Other suitable purging materials can be used instead of or in addition to the virgin PET, the RPET and/or virgin PET/RPET mixture.

In an operation 145, the selected blended virgin PET/RPET mixture of the desired control sample ratio is transferred to a drier (e.g., such as is available from Con Air of Franklin, Pa., carousel drier model CAG 2400 or equivalent). The selected blended virgin PET/RPET mixture can be dried to achieve a desired moisture content. For some thermoplastics, the moisture content is not significant and therefore operation 145 may be optional for those thermoplastics (e.g. polyethylene, polystyrene, polypropylene, etc.). For the virgin PET/RPET mixtures, a moisture content of less than about 20 to about 200 ppm (e.g., about 50 ppm) is desired and can be achieved by drying in the dryer for about 4 hours operating at about 140° C. with a dew point of −40° C. Excess water (e.g., greater than about 50 ppm) can hydrolyze the polymer chains during the melt-extrusion process. The drying process can range from about 140 to about 170 degrees C. for between about 3 to about 7 hours. The preceding settings for the dryer are merely exemplary and higher and lower temperatures are also suitable as are longer and shorter times and higher and lower dew point settings.

In an operation 150, the selected blended, dried virgin PET/RPET mixture is transferred to an extruder (e.g., such as may be available from Reifenhäuser Inc. of Ipswich, Me., reference number RU0200130 or equivalent).

In an operation 155, the extruder produces sheets having a selected thickness (e.g., from less than about 5 mil to about 500 mil or more). In an optional operation 160, the sheets are cut into two sample portions. In an optional operation 165, the first sample portion is optionally coated with a mold release agent (e.g., a food grade silicone emulsion or equivalent e.g., Ivanhoe Industries, Zion, Ill., model number I-SIL 335 EFG, or equivalent) as are commonly used and found on molded PET products such as molded packaging materials.

In an operation 170 an inquiry is made to determine if additional control sample ratios are desired. If additional control sample ratios are required then the method operations continue in an operation 175. In operation 175, subsequent known amount of virgin PET is blended with the crystallized REPT in the second blender to obtain a subsequent selected control sample ratio of virgin PET to RPET and the method and operations continue with operation 135 as described above.

If no additional control sample ratios are required then the method operations continue in an operation 180. In operation 180, the sheets are analyzed as described in more detail below. The analysis can include one or more of differential scanning calorimetry, ultraviolet-visible (UV-Vis) spectroscopy, physical thickness, attenuated total reflectance Fourier transform infrared spectroscopy (ATR-FTIR) and mechanical analysis.

Differential Scanning Calorimetry

A differential scanning calorimetry analysis will be performed on each of the control sample ratios. Best results will include an analysis of multiple samples (e.g., about 2 to about 20) for each of the control sample ratios.

Figure 2A:
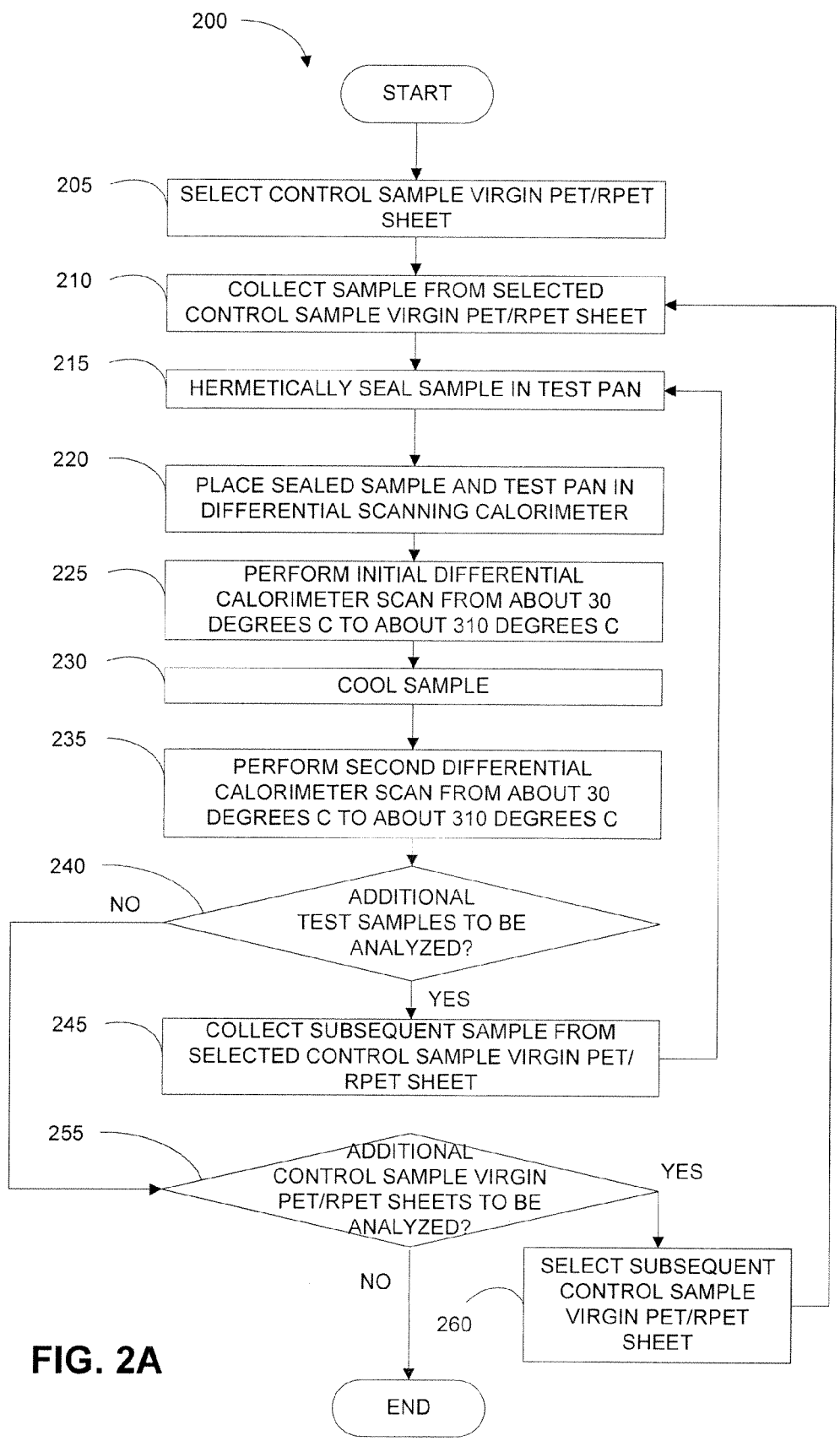
FIG. 2A is a flowchart of the method operations for performing a differential scanning calorimetry analysis for the virgin PET/RPET control samples, in accordance with embodiments of the described invention.

FIG. 2A is a flowchart of the method operations 200 for performing a differential scanning calorimetry analysis for the virgin PET/RPET control samples, in accordance with embodiments of the described invention. The operations illustrated herein are by way of example, as it should be understood that some operations may have sub-operations and in other instances, certain operations described herein may not be included in the illustrated operations. With this in mind, the method and operations 200 will now be described.

In an operation 205, a control sample ratio sheet of virgin PET/RPET is selected. In an operation 210, a first test sample is taken from the selected control sample ratio sheet. The test sample can be between about 3 and about 6 mg of the selected control sample ratio sheet. Smaller or larger test samples can be used but for most differential scanning calorimetry processes approximately 0.1-20 mg is sufficient to yield the needed results. If a differential scanning calorimetry process can test samples even smaller than 0.1 mg, then that is acceptable.

In an operation 215, the test sample is placed in a test pan and hermetically sealed. In an operation 220, the test pan and test sample are placed in a differential scanning calorimeter (e.g., TA Instruments calorimeter model DSCQ1000 available from TA Instruments, of New Castle, Del., or equivalent).

The differential scanning calorimetry analysis includes a first heat cycle, a cool cycle and a second heat cycle between about 30 and about 310 degrees C. at a rate of about 10 degrees C/minute in accordance with ASTM D3418-03 test standards. The differential scanning calorimeter measures and records each of:

a crystallization peak onset ($T_c$ onset)
a crystallization temperature ($T_c$)
a crystallization peak offset ($T_c$ offset)
a crystallization peak width ($T_c$ width)
a heat of crystallization ($\Delta H_c$)
a percent crystallinity
a melting temperature for the first heat cycle ($T_m'$)
a heat of melting for the first heat cycle ($\Delta H_m'$)
a glass transition temperature of the cooling cycle ($T_g$ cool)
a glass transition temperature ($T_g$)
an onset of the melting peak for the second heat cycle ($T_m''$ onset)
a melting temperature of the second heat cycle ($T_m''$)
an offset of the melting peak for the second heat cycle ($T_m''$ offset)
a melting peak width of the second heat cycle ($T_m''$ width); and
a heat of melting for the second heat cycle ($\Delta H_m''$).

The crystallization temperature ($T_c$) is defined as a minimum heat flow of the exothermic peak between the melting temperature and a glass transition temperature. The crystallization temperature has a strong, decreasing linear correlation with RPET composition. Linear regression indicated that the crystallization temperature for the coated PET/RPET sheets follows equation 1 ($R^2$=0.9364). A similar correlation was found for the non-coated samples (equation 2, $R^2$=0.9313).

$$T_{c(coated)} = -0.0478(\% \text{ RPET}) + 139.99° \text{ C.} \quad \text{Equation 1}$$

$$T_{c(non\text{-}coated)} = -0.0561(\% \text{ RPET}) + 140.84° \text{ C.} \quad \text{Equation 2}$$

Figure 2B:
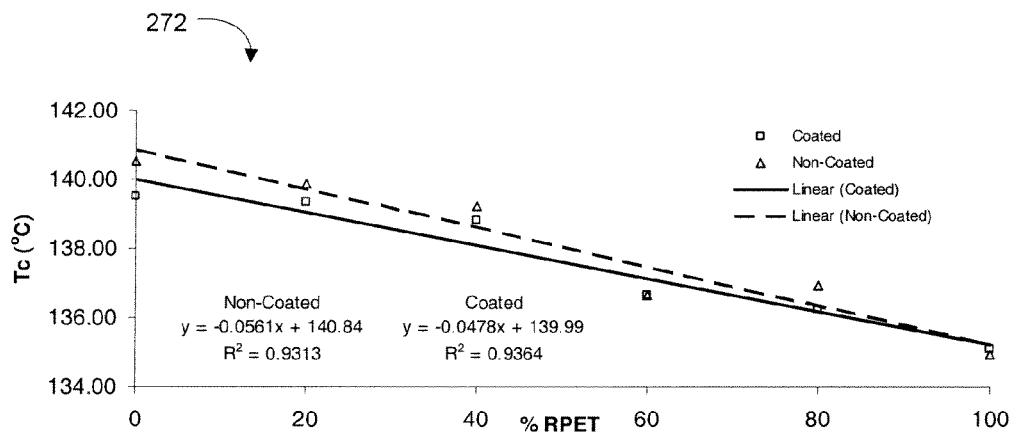
FIG. 2B is a graph of the crystallization temperature ($T_c$), in accordance with embodiments of the described invention.

FIG. 2B is a graph 272 of the crystallization temperature ($T_c$), in accordance with embodiments of the described invention. Statistical analysis (SAS of Cary, N.C.) indicated that the following relationships hold for the coated (P<0.001) and non coated sheets (P<0.001) using Tukey's 95% simultaneous confidence interval. The "C" and "NC" denote the coated and non-coated sheets, respectively.

0C=20C=40C; 0C, 20C, 40C>60C, 80C, 100C; 60C=80C=100C

0NC>60NC, 80NC, 100NC; 20NC=40NC=60NC; 20NC, 40NC>100NC

The data from both the coated and non-coated sheets suggest that the crystallization temperature has potential to be used as a quantitative indicator for the amount of RPET in PET/RPET sheets.

The crystallization peak offset ($T_c$ offset) is determined as an intersection of the tangent line extrapolated from the baseline and tangent line extrapolated from the inflection point of the peak as the signal returns toward the baseline. The data indicated that the crystallization peak offset temperature decreases with increasing amounts of recycled-PET for the coated sheets according to equation 3 ($R^2=0.9864$). A similar trend was found for the non coated sheets (equation 4, $R^2=0.9662$).

$$T_c\text{offset}_{(coated)}=0.0008(\% \text{ RPET})^2-0.1628(\% \text{ RPET})+149.83 \quad \text{Equation 3}$$

$$T_c\text{offseset}_{(non\text{-}coated)}=0.0006(\% \text{ RPET})^2-0.1515(\% \text{ RPET})+149.7 \quad \text{Equation 4}$$

Figure 2C:
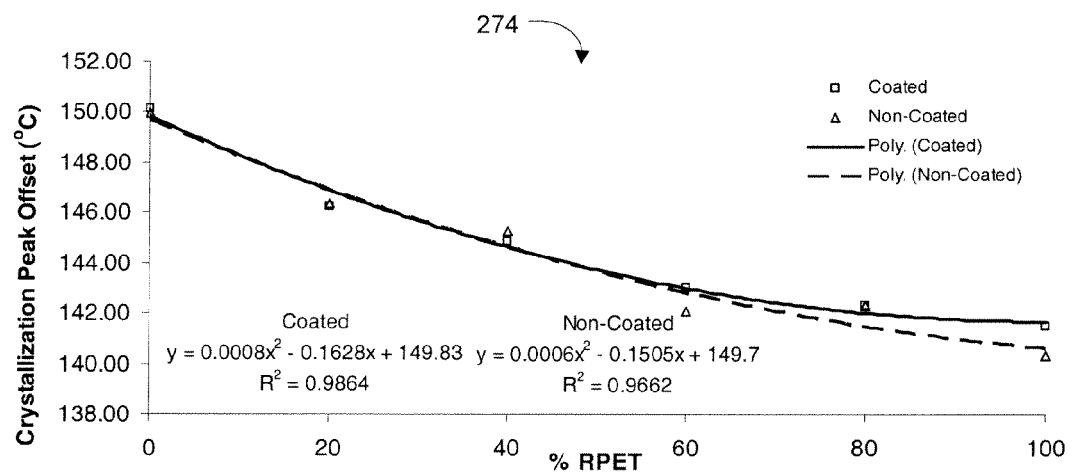
FIG. 2C is a graph of the crystallization peak offset ($T_c$ offset), in accordance with embodiments of the described invention.

FIG. 2C is a graph 274 of the crystallization peak offset ($T_c$ offset), in accordance with embodiments of the described invention. Statistical analysis indicated that the following relationships hold for the coated (P<0.001) and non coated sheets (P=0.007) using Tukey's 95% simultaneous confidence interval. The "C" and "NC" denote the coated and non-coated sheets, respectively:

0C>40C, 60C, 80C, 100C; 0C=20C; 20C>80C, 100C; 40C=60C=80C=100C

0NC>60NC, 80NC, 100NC; 20NC=40NC=60NC=80NC=100NC

It should be noted that there was a high amount of variability in the $T_c$ offset data for the coated 100% virgin sheet. The data from both the coated and non-coated sheets suggest that the crystallization peak offset has the potential to be used as a quantitative indicator for the amount of RPET in PET/RPET sheets.

The crystallization peak width ($T_c$ width) is determined by subtracting the crystallization peak onset from the crystallization peak offset. The data indicated that the crystallization peak becomes narrower as the amount of RPET increases in the sheet. The average values for the PET/RPET sheets were found to have a linear correlation between the crystallization peak width and the % RPET according to equation 5 ($R^2=0.9731$). A similar trend was found for the non-coated sheets (equation 6, $R^2=0.9069$) though to a lesser degree.

$$T_c\text{width}_{(coated)}=-0.047(\% \text{ RPET})+16.09 \quad \text{Equation 5}$$

$$T_c\text{width}_{(non\text{-}coated)}=-0.033(\% \text{ RPET})+14.18 \quad \text{Equation 6}$$

Figure 2D:
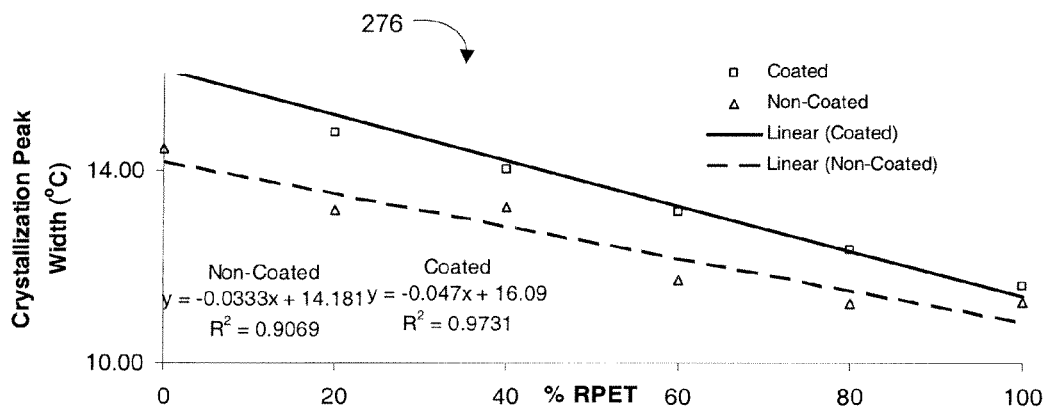
FIG. 2D is a graph of the crystallization peak width ($T_c$ width), in accordance with embodiments of the described invention.

FIG. 2D is a graph 276 of the crystallization peak width ($T_c$ width), in accordance with embodiments of the described invention. Statistical analysis indicated that the following relationships hold for the coated (P=0.010) and non coated sheets (P=0.257) using Tukey's 95% simultaneous confidence interval. The "C" and "NC" denote the coated and non-coated sheets, respectively:

0C=20C=40C; 20C=40C=60C=80C=100C

Similar trends were found for both the coated and the non-coated sheets' average $T_c$ offset values though many of the coated sheets and all $T_c$ offset values of the non-coated sheets were statistically the same. This indicates that $T_c$ offset values are not a quantitative indicator for the selected contaminant (e.g., the mold release coating).

The % crystallinity of each sheet was calculated using equation 7:

$$\% \text{ Crystallinity} = \frac{\Delta H_m - \Delta H_c}{\Delta H_m^o} \times 100\% \quad \text{Equation 7}$$

where $\Delta H_m$, $\Delta H_c$, and $\Delta H_m^o$ (115 J/g)[6] are the enthalpies of melting, crystallization, and melting fully crystalline PET, respectively. These values were calculated by determining the area underneath the peak corresponding to each transition. The data indicated that the percent crystallinity of PET/RPET sheets increases linearly with increasing RPET concentrations as according to equation 8 ($R^2=0.9578$) and equation 9 ($R^2=0.9053$) for the coated and non-coated sheets, respectively.

$$\% \text{ Crystallinity}_{(coated)}=0.0435(\% \text{ RPET})+6.9694 \quad \text{Equation 8}$$

$$\% \text{ Crystallinity}_{(non\text{-}coated)}=0.0444(\% \text{ RPET})+6.7313 \quad \text{Equation 9}$$

Figure 2E:
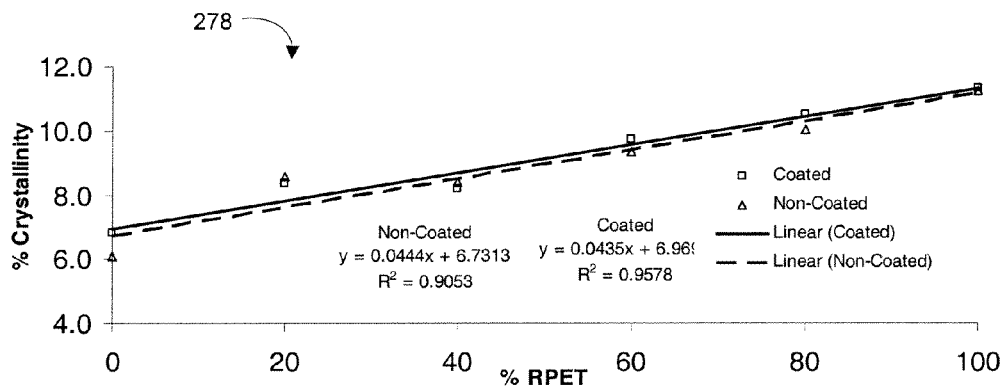
FIG. 2E is a graph of the percent crystallization, in accordance with embodiments of the described invention.

FIG. 2E is a graph 278 of the percent crystallization, in accordance with embodiments of the described invention. Statistical analysis indicated that the following relationships hold for the coated (P<0.001) and non coated sheets (P<0.001) using Tukey's 95% simultaneous confidence interval. The "C" and "NC" denote the coated and non-coated sheets, respectively:

0C<60C, 80C, 100C; 0C=20C=40C; 20C, 40C<80C, 100C; 40=60; 60C=80C=100C

0NC>20NC, 40NC, 60NC, 80NC, 100NC; 20NC>100NC; 20NC=40NC=60NC=80NC

Strong correlations between the average % crystallinity and the amount of recycled-PET in the coated and non-coated sheets were found ($R^2=0.9578$ and $R^2=0.9053$, respectively) with similar plots (equations 8 and 9). However, many of the sheets were not found to be significantly different using a 95% simultaneous confidence interval. The conservativeness of the statistical model indicates that this property has the potential to be used as a quantitative indicator for the amount of recycled-PET in coated and non-coated PET/RPET sheets.

The heat of melting for the first heat cycle ($\Delta H_m'$) is determined by integrating an area between the baseline and the signal of the endothermic peak of the first heat cycle. The data indicated that the heat of melting increases linearly as more RPET is introduced to the PET/RPET sheet. Linear regression indicated that the heat of melting for the first heat cycle increases according to equation 10 ($R^2=0.9468$) for the coated sheets. The correlation between the heat of melting for the first heat cycle was also found for the non-coated sheets though to a lesser degree ($R^2=0.8422$, equation 11).

$$\Delta H_{m(coated)}=0.0525(\% \text{ RPET})+31.745 \quad \text{Equation 10}$$

$$\Delta H_{m(non\text{-}coated)}=0.0383(\% \text{ RPET})+32.691 \quad \text{Equation 11}$$

Figure 2F:
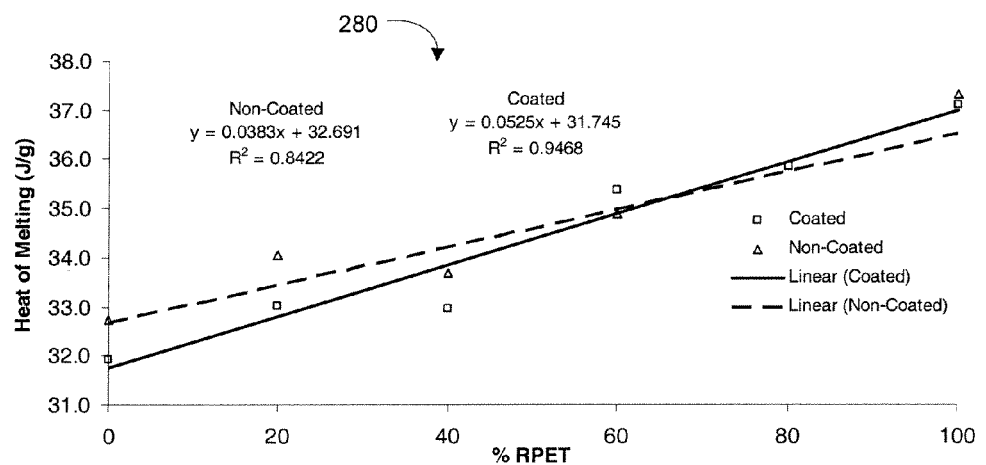
FIG. 2F is a graph of the heat of melting for the first heat cycle ($\Delta H_m'$), in accordance with embodiments of the described invention.

FIG. 2F is a graph 280 of the heat of melting for the first heat cycle ($\Delta H_m'$), in accordance with embodiments of the described invention. Statistical analysis indicated that the following relationships hold for the coated (P<0.001) and non coated sheets (P=0.023) using Tukey's 95% simultaneous confidence interval. The "C" and "NC" denote the coated and non-coated sheets, respectively:

0C<60C, 80C, 100C; 20C, 40C<80C, 100C; 0C=100C

0NC=20NC=40NC=60NC=80NC; 0NC<100NC; 20NC=40NC=60NC=80NC=100NC

A strong correlation between the heat of melting for the first heat cycle and recycled-PET content was found although a few sheet types were statistically the same. All of the non-coated sheets containing recycled-PET were found to be statistically the same using Tukey's 95% simultaneous confidence interval indicating that heat of melting for the first heat cycle is not a quantitative indicator for the selected contaminant (e.g., the mold release coating).

The $T_c$ onset data indicates that the onset of crystallization decreases non-linearly with increasing amounts of recycled content up to 60% RPET then levels off for 80 and 100% RPET sheets. A similar decreasing trend was found for the non-coated PET/RPET sheets. Statistical analysis indicated that the following relationships hold for the coated (P<0.001) and non coated sheets (P<0.001) using Tukey's 95% simultaneous confidence interval. The data from both the C and NC sheets suggest that this property may not be a good quantitative indicator for the amount of RPET in PET/RPET sheets as many of the sheets were statistics the same using Tukey's 95% simultaneous confidence interval; although noticeable trends of the average values were found with $R^2$ values greater than 0.93.

The heat of crystallization ($\Delta H_c$) was determined by integrating the area between the baseline and the signal of the exothermic peak. The data indicated that there was no correlation between the heat of crystallization and of RPET composition. Statistical analysis determined that there is no significant difference between all coated sheets for the heat of crystallization using Tukey's 95% simultaneous confidence interval (P=0.815). All non-coated sheets were also found to be statistically the same (P=0.160).

The melting temperature ($T_m'$) of the first heat cycle was determined to be the maximum signal of the melting endotherm. The data indicated that there is no correlation between the melting temperature of the first heat cycle and the amount of recycled-PET in the sheet. Statistical analysis indicated that the coated 100% virgin sheet was not significantly different from any of the coated sheets containing RPET using Tukey's 95% simultaneous confidence interval, though the 20% RPET sheet was found to be significantly lower than the 80% RPET sheet (P=0.002). The 100% RPET sheet was also found to be significantly higher than the 20%, 40%, and 60% RPET sheets. All of the non-coated sheets were found to be statistically the same (P=0.020) using the statistical model chosen.

The glass transition temperature of the cooling cycle ($T_g$ cooling cycle) was determined as the inflection point of the signal as the polymer cooled from the melt. The data indicated that there is no correlation between the glass transition temperature of the cooling cycle and RPET composition. Statistical analysis indicated that none of the coated sheets were significantly different using Tukey's 95% simultaneous confidence interval (P=0.101). The same behavior was found for the non-coated sheets (P=0.539).

The glass transition temperature ($T_g$) of PET/RPET sheets was determined by differential scanning calorimetry and defined as the inflection point of the signal of the second heat cycle. As with the $T_g$ from the cooling cycle, no correlation was found between the $T_g$ and the amount of RPET in PET/RPET sheets as the glass transition temperature for all sheets were statistically the same using Tukey's 95% simultaneous confidence interval (P=0.115). The non-coated PET/RPET sheets followed the same behavior as the coated sheets, except the 100% virgin and 20% RPET sheets (P=0.462), and all sheets were found to be statistically the same.

The onset to the melting peak ($T_m''$ onset) was determined as the temperature at which the tangent of the baseline and the tangent of the signal at the inflection point intersect. The data from both the coated and non-coated sheets indicated that there is no correlation between the melting peak onset for the second heat cycle and RPET composition in the coated and non-coated sheets. Statistical analysis indicated that the following relationships hold for the coated (P<0.001) and non coated sheets (P=0.001) using Tukey's 95% simultaneous confidence interval.

The melting temperature ($T_m''$) of the second heat cycle was determined to be the maximum signal of the melting endotherm. The data indicated that there is no correlation between the melting temperature of the second heat cycle and the amount of recycled PET in the sheet. Statistical analysis indicated that the following relationships hold for the coated (P<0.001) and non coated sheets (P=0.037) using Tukey's 95% simultaneous confidence interval. A similar trend was observed for the melting temperature of the first heat cycle except the melting temperature of the second heat cycle was approximately 3° C. lower for all sheets suggesting that this property decreases after the first heat cycle. The reduction of the melting temperature of the second heat cycle may be attributed to hydrolysis of the polymer chains from the absorbed atmospheric moisture at elevated temperatures during the first heat cycle. The non-coated PET/RPET sheets had similar behavior as the coated sheets, although all of the non-coated sheets were statistically the same.

Melt polymerized PET contains a free cyclic trimer that can introduce problems due to its migration to the surface of the film or fiber producing irregularities in the final product. During synthesis, an intermolecular ether-forming reaction occurs between the β-hydroxyethyl ester end groups producing diethylene glycol (DEG) which becomes incorporated into the polymer as a co-mononer. PET with DEG (2-3 mol %) will have reduced crystallinity, lower melting point and mechanical properties, less UV stability, and decreased thermo-oxidative resistance. The amount of DEG in the polymer can be calculated after measuring the melting temperature (equation 12).

$$T_m = 271 - 5.5 \times (\text{wt \% } DEG) \quad \text{Equation 12}$$

The weight percent DEG was calculated for the coated and non-coated PET/RPET sheets according to equation 12 (data not shown). As the DEG content is only dependent on the melting temperature, the statistical model indicated the same significant differences as for $T_m''$. The DEG content in the PET/RPET sheets was found to be around 4 wt %.

The melting peak offset of the second heat cycle ($T_m''$ offset) was determined as the intersection of the tangent line extrapolated from the baseline and tangent line extrapolated from the inflection point of the peak as the signal returns toward the baseline. The data indicated that there is no correlation between the melting peak offset of the second heat cycle and RPET composition in the sheet. Statistical analysis indicated that the following relationships hold for the coated (P<0.001) and non coated sheets (P=0.077) using Tukey's 95% simultaneous confidence interval. The non-coated PET/RPET sheets had similar behavior as the coated sheets for the melting peak offset, although all of the non-coated sheets were statistically the same.

Figure 2G:
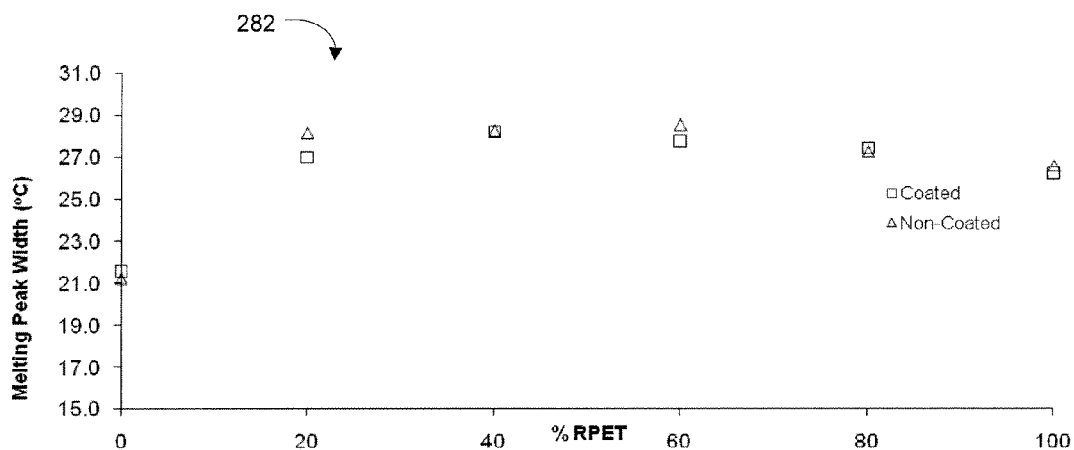
FIG. 2G is a graph of the melting peak width ($T_m''$ width), in accordance with embodiments of the described invention.

The melting peak width ($T_m''$ width) was determined by subtracting the melting peak onset from the melting peak offset. FIG. 2G is a graph 282 of the melting peak width ($T_m''$ width), in accordance with embodiments of the described invention. The data indicated that there is no correlation between the melting peak width of the second heat cycle and the amount of RPET in the sheet. Statistical analysis indicated that the following relationships hold for the coated (P<0.001) and non coated sheets (P<0.001) using Tukey's 95% simultaneous confidence interval. The non-coated PET/RPET sheets had similar behavior as the coated sheets for the melting peak width of the second heat cycle, although all of the non-coated sheets containing recycled-PET were statistically the same.

The heat of melting ($\Delta H_m''$) was determined by integrating the area between the baseline and the signal of the endothermic peak of the second heat cycle. The data indicated that the heat of melting for the second heat cycle did not have a strong correlation with the amount of RPET as the heat of melting for the first heat cycle. Statistical analysis indicated that the following relationships hold for the coated (P<0.001) and non coated sheets (P=0.294) using Tukey's 95% simultaneous confidence interval.

Referring again to FIG. 2A, in an operation 225, the differential scanning calorimeter analyzes the test sample in an the initial heat cycle to obtain the $T_c$ onset, $T_c$, $T_c$ offset, $T_c$ width, $\Delta H_c$, percent crystallinity, $T_m'$, and $\Delta H_m'$.

In an operation 230, the test sample is allowed to cool at a rate of about 10 degrees C. per minute. In an operation 235, a second heat cycle obtains the $T_m''$ onset, $T_m''$, $T_m''$ offset, $T_m''$ width, and $\Delta H_m''$.

In an operation 240, if additional test samples of the selected control sample ratio remain to be tested, then the method operations continue in an operation 245. In operation 245 a subsequent test sample is taken from the selected control sample ratio sheet and the method operations continue in operation 215 as described above. As described above, multiple samples of each control sample ratio are analyzed. By way of example, five test samples per each virgin PET/RPET ratio sheet were analyzed.

In operation 240, if no additional test samples of the selected control sample ratio remain to be tested, then the method operations continue in an operation 255. In operation 255, if additional control sample ratios remain to be tested, then the method operations continue in an operation 260. In operation 260, a subsequent control sample ratio sheet is selected and the method operations continue in operation 210 as described above. In operation 255, if no additional control sample ratios remain to be tested, then the method operations can end.

Physical Thickness

Figure 3:
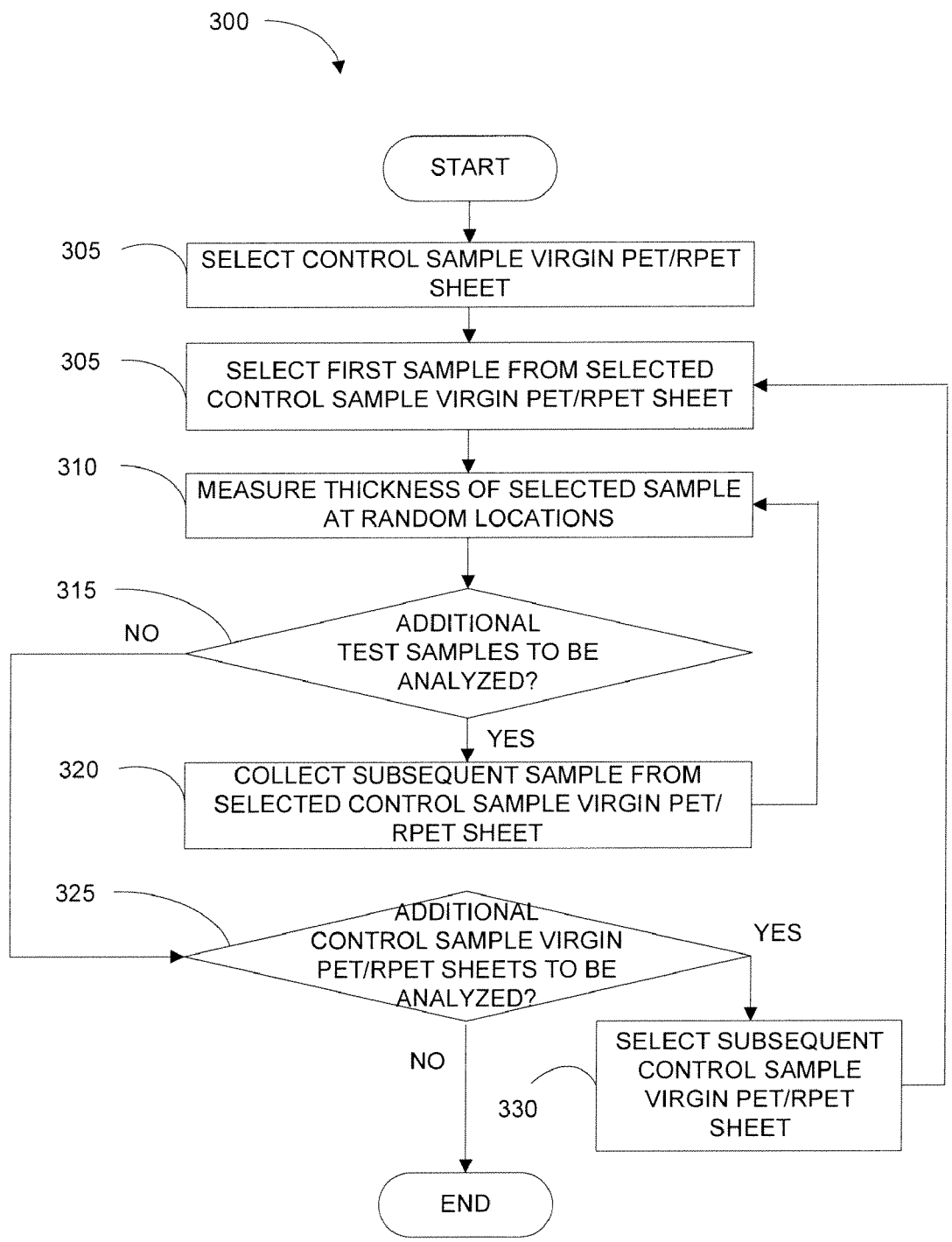
FIG. 3 is a flowchart of the method operations for measuring the physical thickness for the virgin PET/RPET control samples, in accordance with embodiments of the described invention.

Consistency of physical thickness is another aspect of the content of a sheet of virgin PET/RPET. FIG. 3 is a flowchart of the method operations 300 for measuring the physical thickness for the virgin PET/RPET control samples, in accordance with embodiments of the described invention. The operations illustrated herein are by way of example, as it should be understood that some operations may have sub-operations and in other instances, certain operations described herein may not be included in the illustrated operations. With this in mind, the method and operations 300 will now be described.

In an operation 305, a control sample ratio sheet of virgin PET/RPET is selected. In an operation 310, a first test sample is taken from the selected control sample ratio sheet.

In an operation 315 a thickness of the selected test sample is measured and recorded. The thickness of the test sample can be measured as many times as desired but at least once. The thickness is measured at random locations on the selected test sample. By way of example the thickness of the test sample can be measured between 1 and about 100 random locations (e.g., 12 locations).

In an operation 320, if additional test samples of the selected control sample ratio remain to be tested, then the method operations continue in an operation 325. In operation 325 a subsequent test sample is taken from the selected control sample ratio sheet and the method operations continue in operation 315 as described above. As described above, multiple samples of each control sample ratio sheet are measured. By way of example, five test samples per each control sample ratio sheet can be measured.

In operation 330, if no additional test samples of the selected control sample ratio remain to be tested, then the method operations continue in an operation 335. In operation 335, if additional control sample ratio sheets remain to be tested, then the method operations continue in an operation 340. In operation 340, a subsequent control sample ratio sheet is selected and the method operations continue in operation 310 as described above. In operation 335, if no additional control sample ratio sheets remain to be tested, then the method operations can end.

Ultraviolet-Visible Spectroscopy

Ultraviolet-visible (UV-Vis) spectroscopy is used to determine an absorption behavior of each virgin PET/RPET sheet in the UV-Vis regions of the spectrum. Each control sample ratio sheet is scanned between 200-700 nm using a UV-Vis spectrometer (e.g., a Shimadzu Pharmaspec UV-1700 UV-Vis spectrometer, or equivalent) set to a single scan mode at medium speed with a sampling interval of about 1.0 nm.

Figure 4A:
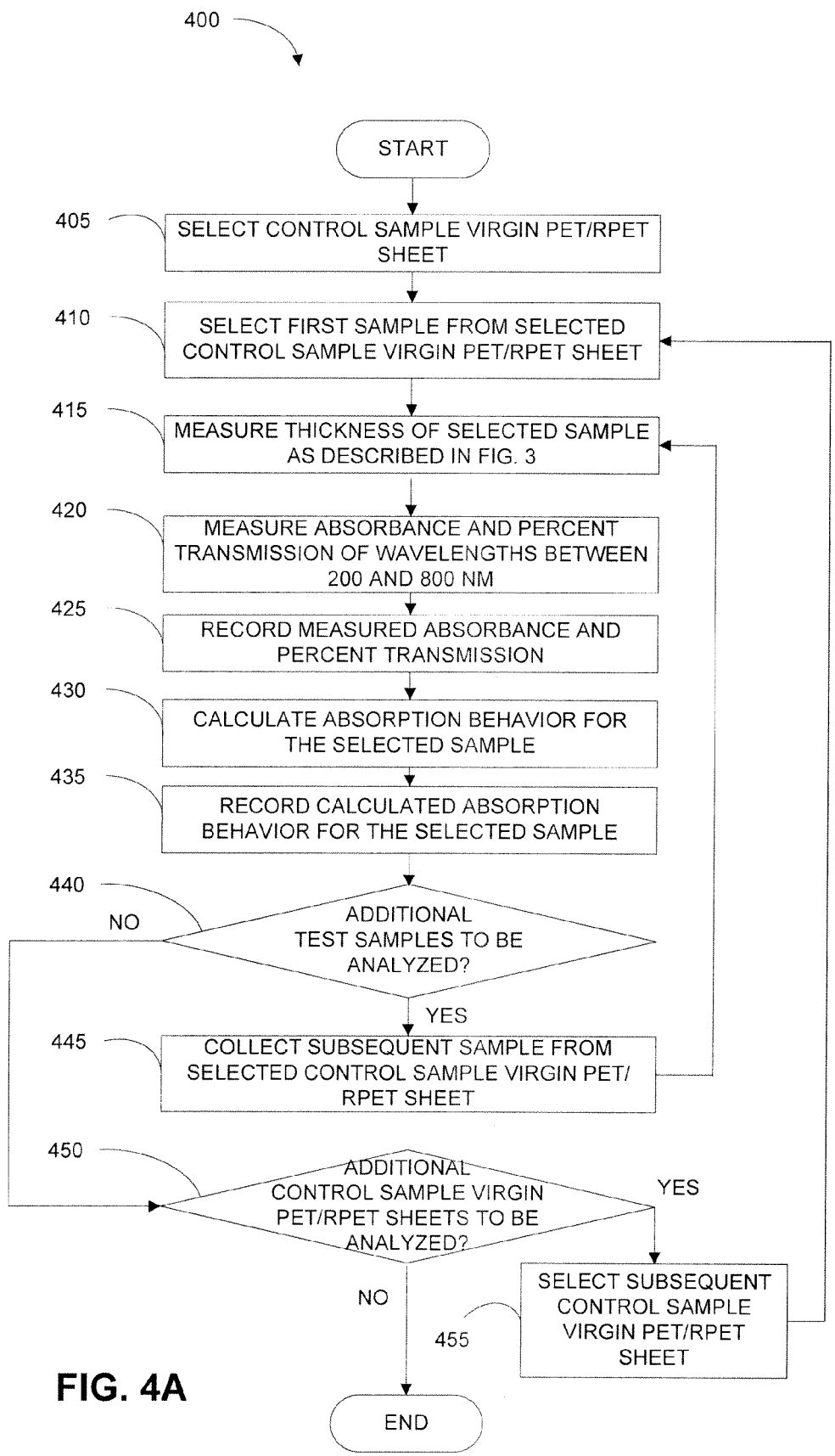
FIG. 4A is a flowchart of the method operations for performing an ultraviolet-visible (UV-Vis) spectroscopy analysis for the virgin PET/RPET control samples, in accordance with embodiments of the described invention.

FIG. 4A is a flowchart of the method operations 400 for performing an ultraviolet-visible (UV-Vis) spectroscopy analysis for the virgin PET/RPET control samples, in accordance with embodiments of the described invention. The operations illustrated herein are by way of example, as it should be understood that some operations may have sub-operations and in other instances, certain operations described herein may not be included in the illustrated operations. With this in mind, the method and operations 400 will now be described.

In an operation 405, a control sample ratio sheet of virgin PET/RPET is selected. In an operation 410, a first test sample is taken from the selected control sample ratio sheet. In an operation 415, the thickness of the selected sample is measured as described in FIG. 3 above.

In an operation 420, the selected test sample is scanned between about 200 to about 800 nm. At least one wavelength (e.g., about 350 nm) is scanned. However, many wavelengths between about 200 to about 800 nm can be scanned. The results of each scan at each wavelength is recorded in an operation 425.

In an operation 430, the recorded results are divided by the thickness determined in operation 415 to produce a normalized absorption behavior for the selected sample. In an operation 435, the absorption behavior for the selected sample is recorded.

Figure 4B:
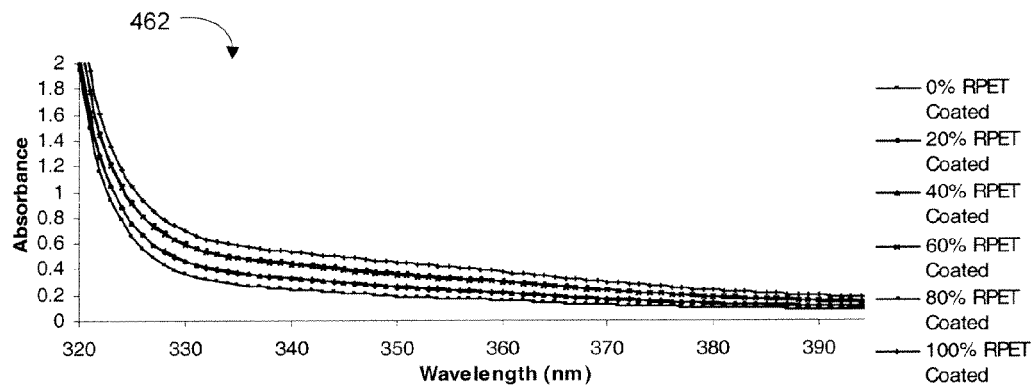
FIG. 4B is a graph of the absorbance, in accordance with embodiments of the described invention.

Statistical analysis indicated that the absorbance values for all coated and non-coated PET/RPET sheets are significantly different using Tukey's 95% simultaneous confidence interval indicating that the absorbance at 350 nm has potential to be used as a quantitative indicator for the amount of RPET in PET/RPET sheets. FIG. 4B is a graph 462 of the absorbance, in accordance with embodiments of the described invention. It should be noted that the silicone coating did not noticeably affect the absorbance values at 350 nm as the trend lines of the average values are similar (equations 13 and 14).

Figure 4C:
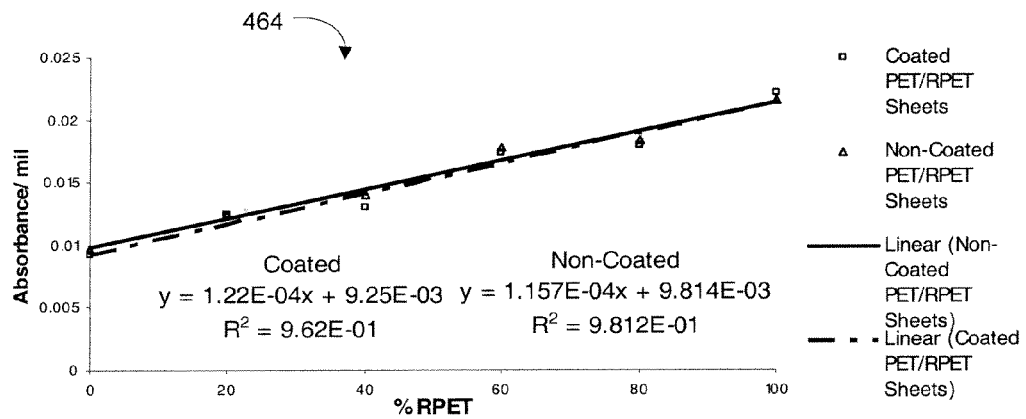
FIG. 4C is a graph of the absorbance per mil, in accordance with embodiments of the described invention.
Figure 4D:
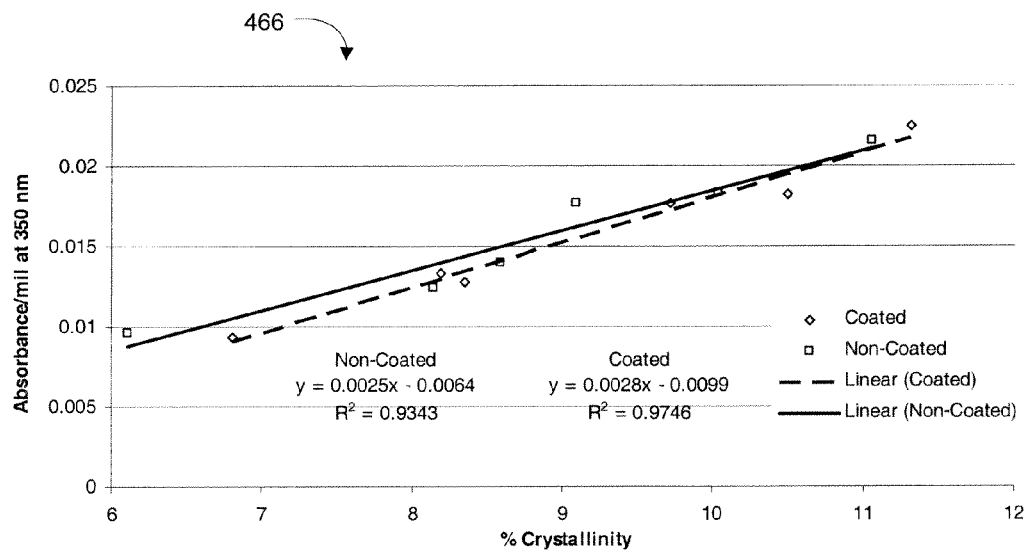
FIG. 4D is a graph of the absorbance per mil at 350 nm, in accordance with embodiments of the described invention.
Figure 8:
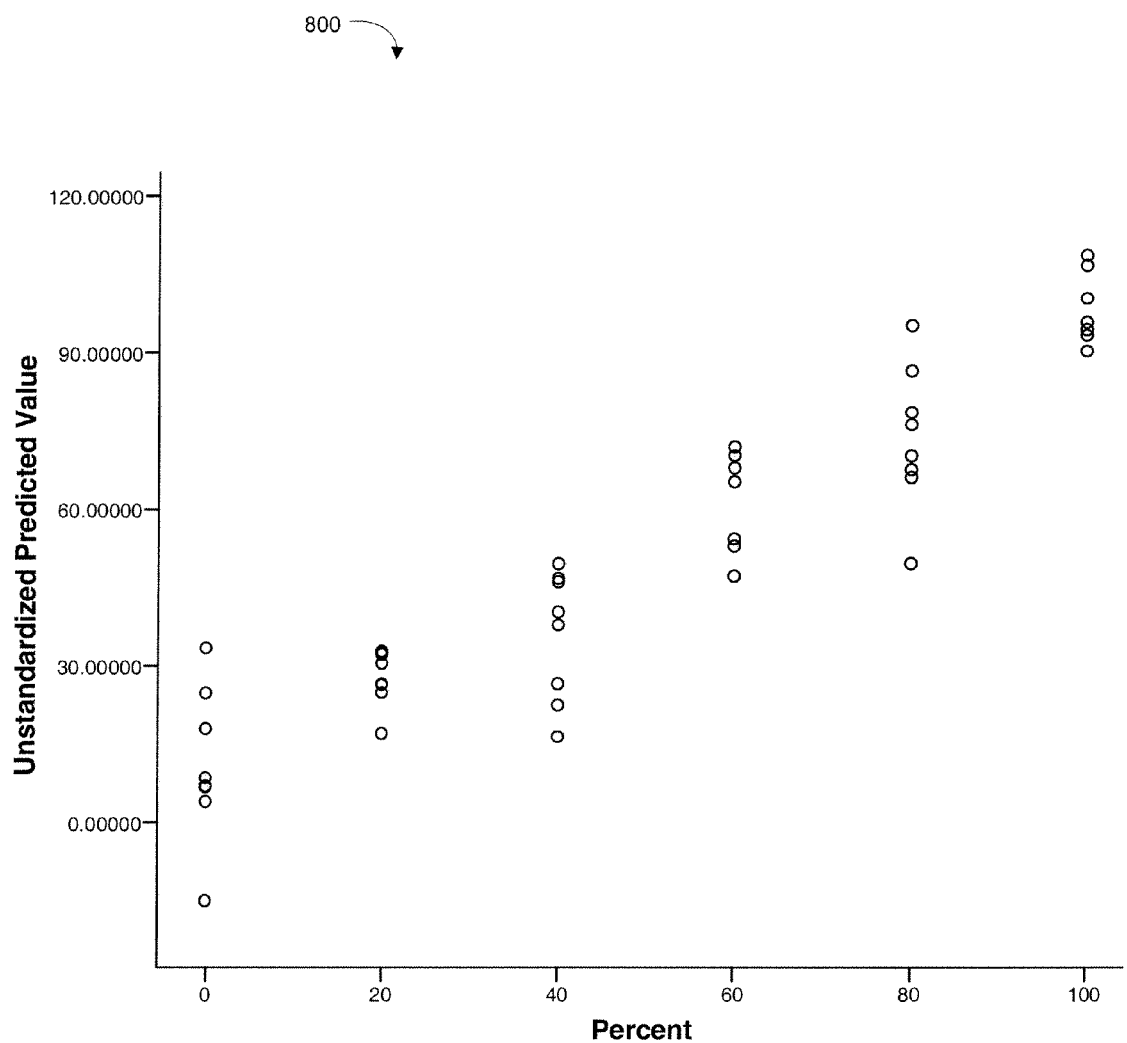
FIG. 8 is a graph of a % RPET and a predicted % RPET, in accordance with embodiments of the described invention.

FIG. 4C is a graph 464 of the absorbance per mil (0.001 inches, 0.0254 millimeters), in accordance with embodiments of the described invention. FIG. 4D is a graph 466 of the absorbance per mil at 350 nm, in accordance with embodiments of the described invention. The increase in absorbance at 350 nm had a strong linear correlation with the increase in % crystallinity for both the coated and non-coated sheet types (FIG. 8, equations 15 and 16, respectively).

$$A_{350nm(coated)} = 1.22 \times 10^{-4} (\% \text{ RPET}) + 9.25 \times 10^{-1} \quad \text{Equation 13}$$

$$A_{350nm(non\text{-}coated)} = 1.16 \times 10^{-4} (\% \text{ RPET}) + 9.81 \times 10^{-3} \quad \text{Equation 14}$$

$$A_{350nm(coated)} = 0.0028 (\% \text{ Crystallinity}) - 0.0099 \quad \text{Equation 15}$$

$$A_{350nm(non\text{-}coated)} = 0.0025 (\% \text{ Crystallinity}) - 0.0064 \quad \text{Equation 16}$$

Referring again to FIG. 4A, in an operation 440, if additional test samples of the selected control sample ratio remain to be tested, then the method operations continue in an operation 445. In operation 445 a subsequent test sample is taken from the selected control sample ratio sheet and the method operations continue in operation 415 as described above. As described above, multiple samples of each control sample ratio sheet are measured. By way of example, five test samples per each control sample ratio sheet can be measured.

In operation 440, if no additional test samples of the selected control sample ratio remain to be tested, then the method operations continue in an operation 450. In operation 450, if additional control sample ratio sheets remain to be tested, then the method operations continue in an operation 455. In operation 455, a subsequent control sample ratio sheet is selected and the method operations continue in operation 410 as described above. In operation 450, if no additional control sample ratio sheets remain to be tested, then the method operations can end.

Attenuated Total Reflectance Fourier Transform-Infrared Spectroscopy

Attenuated total reflectance Fourier transform infrared spectroscopy (ATR-FTIR) qualitatively determines a presence of various functional groups and conformations of the selected polymer for each control sample ratio sheet. A Smart Performer ATR assembly (Thermo Scientific of Waltham, Me., or equivalent) attached to a Nexus 470 Fourier Transform Infrared Spectrometer (Nicolet Instruments of Offenbach, Del., or equivalent) can scan test samples at 32 scans per analysis.

Figure 5A:
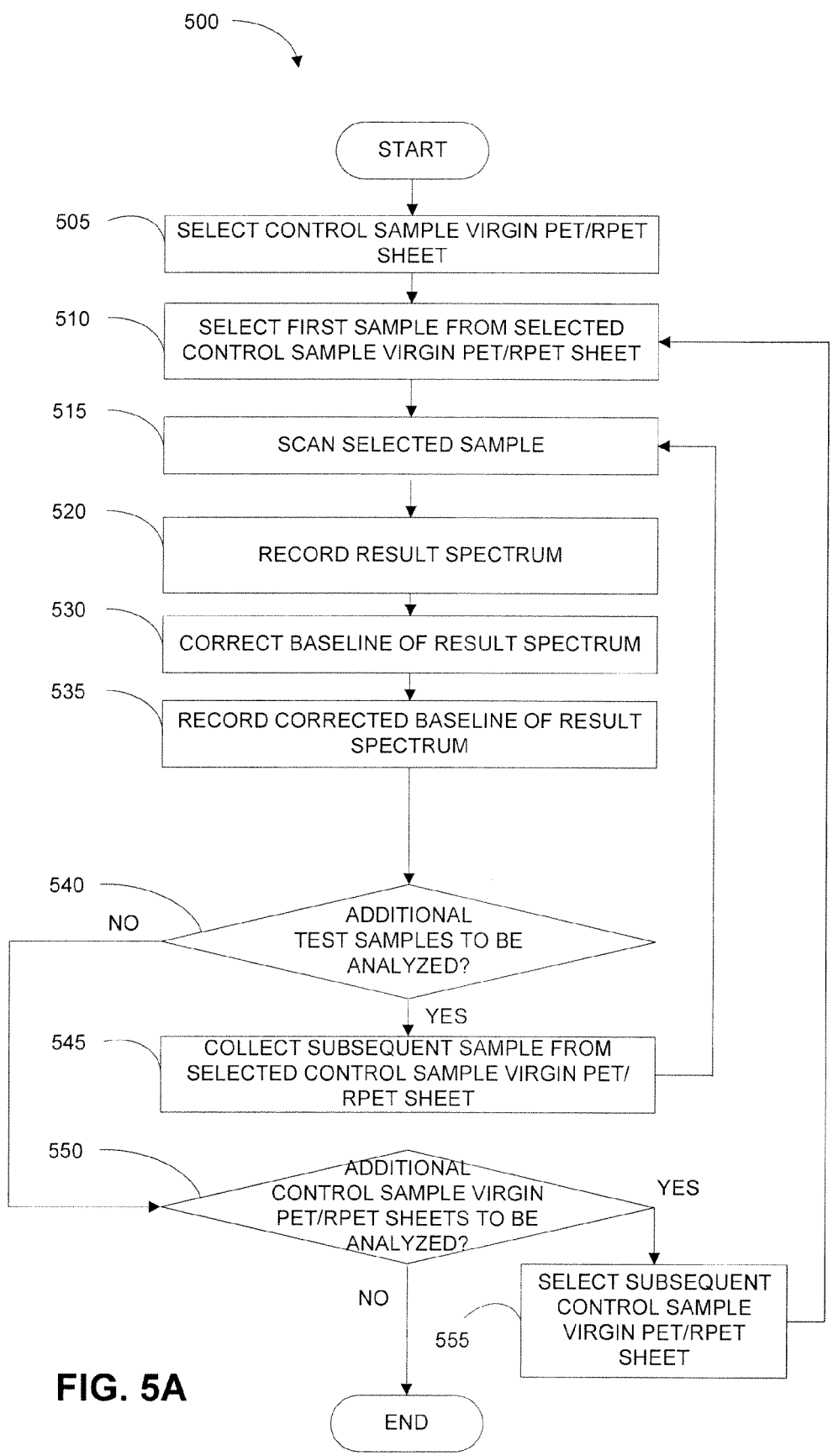
FIG. 5A is a flowchart of the method operations for performing an attenuated total reflectance Fourier transform infrared spectroscopy (ATR-FTIR) analysis for the virgin PET/RPET control samples, in accordance with embodiments of the described invention.

FIG. 5A is a flowchart of the method operations 500 for performing an attenuated total reflectance Fourier transform infrared spectroscopy (ATR-FTIR) analysis for the virgin PET/RPET control samples, in accordance with embodiments of the described invention. The operations illustrated herein are by way of example, as it should be understood that some operations may have sub-operations and in other instances, certain operations described herein may not be included in the illustrated operations. With this in mind, the method and operations 500 will now be described.

In an operation 505, a control sample ratio sheet of virgin PET/RPET is selected. In an operation 510, a first test sample is taken from the selected control sample ratio sheet.

In an operation 515, the selected test sample is scanned between about 650 and 4000 wavenumbers with a resolution of about 1 wavenumber. A result spectrum of each scan is recorded in an operation 520.

In an operation 530, a baseline of each recorded result spectrum is corrected by Omnic software (version 5.1 Nicolet Instruments of Offenbach, Del.). In an operation 535, the corrected result spectrum of each scan is recorded. The results of the analysis can include a wandering baseline yielding absorbance values higher than they should be. As a result, the baseline is corrected. The wandering baseline could be caused by the physical conditions of the sample or the apparatus.

In an operation 540, if additional test samples of the selected control sample ratio remain to be tested, then the method operations continue in an operation 545. In operation 545 a subsequent test sample is taken from the selected control sample ratio sheet and the method operations continue in operation 515 as described above. As described above, multiple samples (e.g., between about 2 and about 20) of each control sample ratio sheet are measured. By way of example, three test samples per each control sample ratio sheet can be measured.

In operation 540, if no additional test samples of the selected control sample ratio remain to be tested, then the method operations continue in an operation 550. In operation 550, if additional control sample ratio sheets remain to be tested, then the method operations continue in an operation 555. In operation 555, a subsequent control sample ratio sheet is selected and the method operations continue in operation 510 as described above. In operation 550, if no additional control sample ratio sheets remain to be tested, then the method operations can end.

Figure 5B:
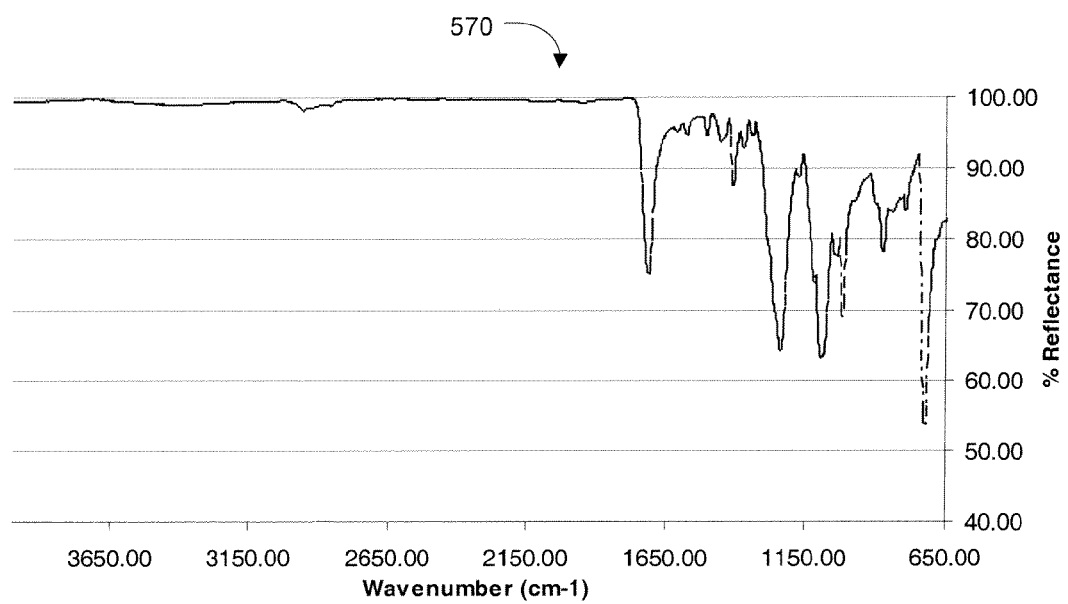
FIG. 5B is a graph of the Fourier transform-infrared spectroscopy, in accordance with embodiments of the described invention.

Fourier transform-infrared spectroscopy can also be used to characterize the conformations of amorphous and crystalline regions of the polymer. Absorptions at 896 and 973 cm$^{-1}$ have been attributed to the gauche and trans conformations of the EG units, respectively. In the amorphous regions, the EG units are in the gauche conformer which transforms into mostly trans conformers during orientation (mesomorphic amorphous state). The gauche conformation of the EG unit transforms into the trans-gauche conformer during chain orientation, increasing crystallization. All EG conformations transform to the trans-conformation at a critical degree in the crystalline region. The FTIR spectrum that was the most consistent within each sheet type was used for comparison against other sheet types. The peak minimums were used to determine the molecular composition and conformations of the polymer chain. FIG. 5B is a graph 570 of the Fourier transform-infrared spectroscopy, in accordance with embodiments of the described invention.

TABLE 1

| Wavenumber (cm$^{-1}$) | Representation |
|---|---|
| 723 | Flexion of aromatic ring |
| 792 | Flexion of aromatic ring |
| 840 | Trans conformation of EG group |
| 871 | Gauche conformation of EG group |
| 1016 | Balancing of C—H in the CH$_2$ group |
| 1039 | Gauche conformation of EG group |
| 1087 | C—O extension of alcohol end groups |
| 1116 | Symmetric extension of C—O—C in ester group |
| 1174 | Associated with the EG group |
| 1240-1330 | Associated with parallel dichroism |
| 1340 | Extended-trans conformation in crystalline region; flexion of the ethyl unit |
| 1371 | Relaxed-gauche conformation in amorphous region; flexion of the ethyl unit |
| 1407 | Flexion of O—H in alcohol end groups |
| 1452 | Gauche-conformation of the EG group |
| 1504 | Flexion of aromatic ring |
| 1577 | Aromatic ring vibration |
| 1612 | Aromatic ring vibration |
| 1712 | Carbonyl extension |
| 2958 | Extension of C—H of aromatic ring |

Mechanical Analysis

The mechanical analysis of the mechanical properties of each control sample ratio sheet were evaluated in a lengthwise (i.e., machine) direction and in a transverse direction substantially perpendicular to the machine direction. The mechanical analysis can be performed with a Testometric Universal Testing Machine (Model M350-5 kN, from Testometric of the United Kingdom, or equivalent) equipped with a 500 kgf load cell in the tensile mode. The Testometric Universal Testing Machine has a capacity of 5 kN with an accuracy of ±0.5%. The stress and strain at the proportional limit (PL), yield stress and strain, and Young's Modulus were calculated from the force-deformation curves obtained from multiple test specimens per PET/RPET sheet type in the machine and transverse directions.

Figure 6:
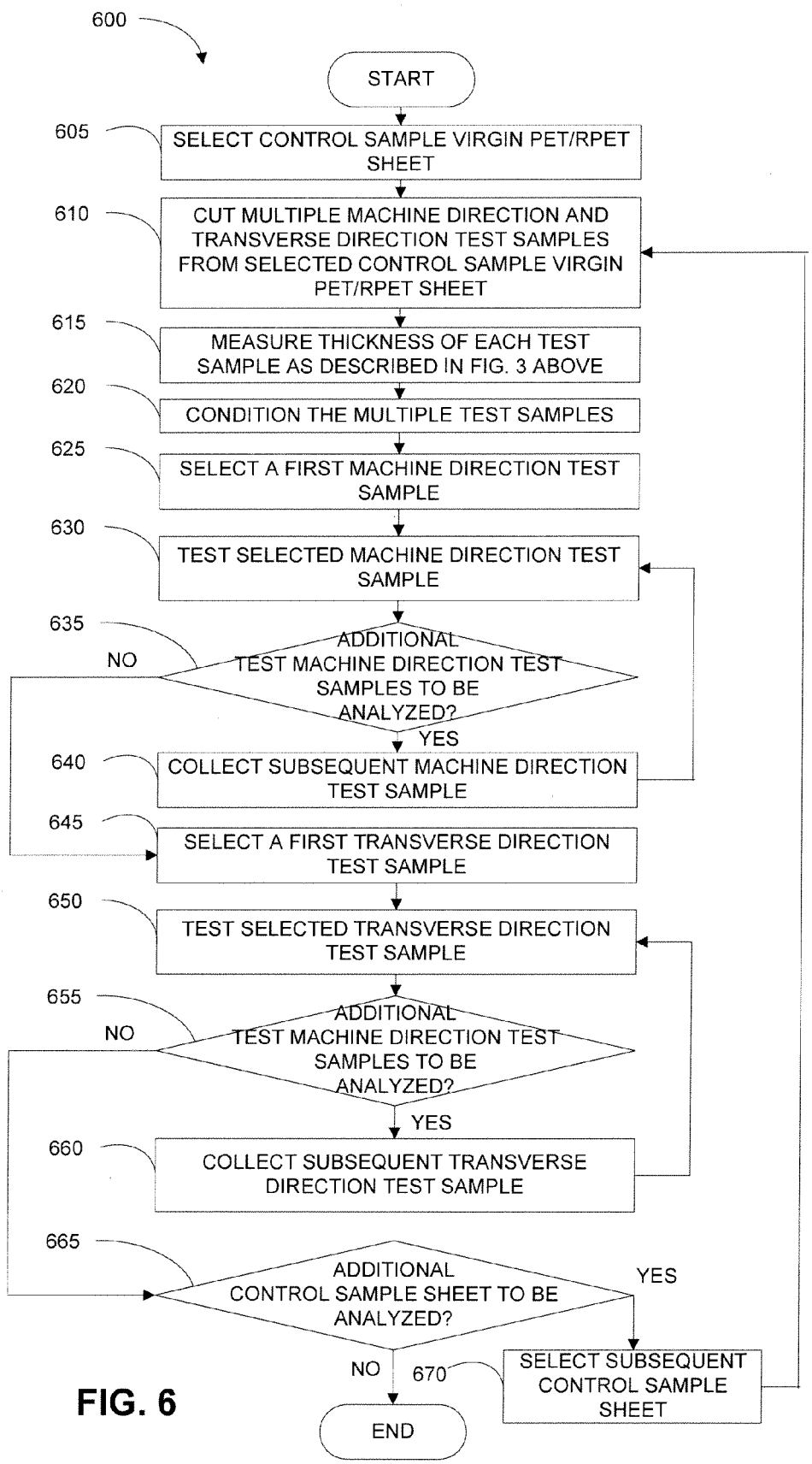
FIG. 6 is a flowchart of the method operations for performing a mechanical analysis for the virgin PET/RPET control samples, in accordance with embodiments of the described invention.

FIG. 6 is a flowchart of the method operations 600 for performing a mechanical analysis for the virgin PET/RPET control samples, in accordance with embodiments of the described invention. The operations illustrated herein are by way of example, as it should be understood that some operations may have sub-operations and in other instances, certain operations described herein may not be included in the illustrated operations. With this in mind, the method and operations 600 will now be described.

In an operation 605, a control sample ratio sheet of virgin PET/RPET is selected. In an operation 610, a multiple test samples are taken from the selected control sample ratio sheet. Approximately 50% of the test samples are cut in the machine direction and approximately 50% are cut in the transverse direction. The machine direction is the direction the thermoplastic sheet is extruded from the extruder. The transverse direction is substantially perpendicular to the machine direction. Test samples can be cut with a JDC specimen cutter Model—25 (Thwing-Albert Instrument Company, USA, or equivalent) having a width of about 1.000±0.001 inch (2.54 cm), and about 6 (20.3 cm) in length. Other test specimen sizes are acceptable, but must be noted to correctly perform the calculations. In an operation 615, the thickness of each test sample is measured as described in FIG. 3 above.

In an operation 620, the multiple test specimens are conditioned for a selected time period. By way of example, the selected test specimen can be conditioned for 40 hours. Conditioning allows all of the test specimens to achieve the same temperature and relative humidity before testing. By way of example, the test specimen can be conditioned at 23 degrees C. with a 50% relative humidity in accordance with ASTM D882-02.

In an operation 625, a first conditioned, machine direction test specimen is selected. In an operation 630, the selected machine direction test specimen is tested in the machine direction. The rate of grip separation can be about 50.0 mm/min with an initial strain rate of 0.5 mm/(mm·min) and a gauge length of 2 inches (5.1 cm). A stress and strain at the proportional limit (PL) and yield point are determined.

In an operation 635, if additional machine direction, conditioned test specimens are available for testing, then a subsequent machine direction conditioned test sample is selected in an operation 640 and the method operations continue in operation 630 as described above.

In operation 635, if additional machine direction, conditioned test specimens are not available for testing, then the method operations continue in an operation 645.

In operation 645, a first conditioned, transverse direction test specimens is selected. In an operation 650, the selected transverse direction test specimen is tested in the transverse direction in a similar manner to the machine direction testing described in operation 630 above.

In an operation 655, if additional transverse direction, conditioned test specimens are available for testing, then a subsequent machine direction conditioned test specimen is selected in an operation 660 and the method operations continue in operation 650 as described above.

In operation 655, if additional machine direction, conditioned test specimens are not available for testing, then the method operations continue in an operation 665.

In an operation 665, an elastic modulus for the selected control sample ratio sheet is calculated from a set of force-deformation curves obtained from the machine direction and transverse direction test specimens.

In an operation 670, if additional control sample ratio sheets remain to be tested, then the method operations continue in an operation 675. In operation 675, a subsequent control sample ratio sheet is selected and the method operations continue in operation 610 as described above. In operation 670, if no additional control sample ratio sheets remain to be tested, then the method operations can end.

The proportional limit is defined as when the stress and strain relationship is no longer linear (Hooke's Law). The stress at the proportional limit increased with increasing RPET content up to 60% then slowly decreased for the 80% and 100% sheets (Table 2). The increase of this property for sheets containing recycled-PET may be attributed to the increasing amount of crystallinity in the sheet indicated by DSC. The increasing concentration of shorter polymer chains (RPET) lubricate the higher molecular weight virgin resin by introducing more free volume in the amorphous regions which competes with the increase in strength due to crystallinity. The increasing free volume allows the polymer chains to expand more easily while still following Hooke's Law. The decrease in the stress at the proportional limit for the 80% and 100% sheets can be attributed to a higher concentration of lower molecular weight chains which posses lower mechanical properties than virgin material. Statistical analysis indicated that the following relationships hold for the stress at the proportional limit of PET/RPET sheets in the machine direction (P<0.001) using Tukey's 95% simultaneous confidence interval.

> 0% RPET<20% RPET, 40% RPET, 60% RPET, 80% RPET, 100% RPET; 20% RPET=80% RPET, 100% RPET; 40% RPET=60% RPET=80% RPET>100% RPET

The data indicated that introducing recycled-PET into PET sheets can increase the amount of stress that the sheet can handle before deviation from Hooke's Law at certain concentrations.

The strain at the proportional limit increased with increasing amounts of recycled-PET although a maximum was reached when the sheet contains 80% RPET (Table 2). Again, the increase of this property for sheets containing recycled-PET may be attributed to a higher molecular weight distribution increasing the plasticizing effect. At 100% RPET, the plasticizing effect disappears and the strain at the proportional limit decreased. The optimum amount of RPET in PET/RPET sheets can be determined by calculating Young's Modulus (discussed later). Statistical analysis indicated that the following relationships hold for the strain at the proportional limit of PET/RPET sheets in the machine direction (P<0.001) using Tukey's 95% simultaneous confidence interval.

> 0% RPET<40% RPET, 60% RPET, 80% RPET, 100% RPET; 0% RPET=20% RPET; 20 RPET %, 40 RPET %<60% RPET, 80% RPET; 20% RPET=40% RPET; 60% RPET=80% RPET

The yield point was defined as the first point on the stress-strain curve where the first derivative equals zero. The stress at the yield point followed a similar trend as the stress at the proportional limit except the yield stress for the 100% RPET sheet was nearly the same as the 80% RPET sheet (Table 2). This behavior can again be explained by the changes in free volume and crystallinity as described above. Statistical analysis indicated that the following relationships hold for the yield stress of PET/RPET sheets in the machine direction (P<0.001) using Tukey's 95% simultaneous confidence interval.

0% RPET<20% RPET, 40% RPET, 60% RPET, 80% RPET, 100% RPET; 20% RPET=40% RPET=60% RPET=80% RPET=100% RPET

The yield strain was found to increase linearly according to equation 17 ($R^2$=0.9072):

YieldStrain=0.0031(% RPET)+0.0607  Equation 17

Statistical analysis indicated that the following relationships hold for the yield strain of PET/RPET sheets in the machine direction (P<0.001) using Tukey's 95% simultaneous confidence interval; however, the conservativeness of the statistical model indicates that the yield strain is not a quantitative indicator for the selected contaminant (e.g., the mold release coating) but could be for other thermoplastics or other selected contaminants.

0% RPET<60% RPET, 80% RPET, 100% RPET; 20% RPET=40% RPET; 20% RPET, 40% RPET>80% RPET, 100% RPET; 60% RPET=80% RPET=100% RPET

The Young's Modulus (YM) was determined by dividing the stress by the strain at the proportional limit and describes the stiffness of sheet. The YM increased steadily with increasing RPET levels up to 40% then dropped sharply below the 100% virgin sheet to the minimum observed value when the sheet contained 80% RPET (Table 2). The steady increase in YM may be attributed to the increase in crystallinity, increasing the strength, with smaller increases in strain due to the higher crystallinity. The drastic drop in YM may be attributed to the strain increasing as a result of more free volume and a decrease in the yield stress values which is attributed to higher concentrations of lower molecular weight chains.

Statistical analysis indicated that the following relationships hold for the Young's Modulus of PET/RPET sheets in the machine direction (P<0.001) using Tukey's 95% simultaneous confidence interval. This indicates that the stiffness of the sheet in the machine direction can be increased or decreased by introducing varying amounts of recycled-PET.

40% RPET>0% RPET>80% RPET; 20% RPET, 40% RPET>60% RPET, 80% RPET, 100% RPET; 60% RPET, 100% RPET>80% RPET; 60% RPET=80% RPET

TABLE 2

| Sample | Stress (MPa) @ LOP | Strain @ LOP | Stress (MPa) @ Yield | Strain @ Yield | Young's Modulus (MPa) |
|---|---|---|---|---|---|
| 0% | 46.7 | 0.0432 | 54.9 | 0.0605 | 1083 |
| 20% | 48.0 | 0.0439 | 56.5 | 0.0616 | 1094 |
| 40% | 48.9 | 0.0442 | 57.1 | 0.0617 | 1105 |
| 60% | 48.9 | 0.0455 | 57.1 | 0.0628 | 1074 |
| 80% | 48.6 | 0.0462 | 56.7 | 0.0636 | 1053 |
| 100% | 47.8 | 0.0446 | 56.8 | 0.0634 | 1072 |

The limit of proportion properties were measured in the transverse direction with the same parameters as the machine direction. A similar maximum stress value in the machine direction was found in the transverse direction, except the sheets with higher RPET concentrations (80% and 100% RPET) had lower values than the 100% virgin sheet (Table 3). This may be attributed to the mechanical orientation that occurs during extrusion in the machine direction aligning the crystalline regions.

Statistical analysis indicated that the following relationships hold for the stress at the proportional limit of PET/RPET sheets in the transverse direction (P<0.001) using Tukey's 95% simultaneous confidence interval.

0% RPET<20% RPET, 40% RPET, 60% RPET; 0% RPET>100% RPET; 20% RPET, 40% RPET

The strain values at the proportional limit in the transverse direction did not follow the same behavior as the strain at proportional limit in the machine direction (Table 3). The strain at the proportional limit in the transverse direction had a steady increase followed by a steep reduction in strain at 40% of recycled-PET, where the strain values increased up to 80% RPET in the machine direction. The 40% RPET sheet held the maximum amount of strain while obeying Hooke's Law and was significantly higher than all other sheet types. Statistical analysis indicated that the following relationships hold for the strain at the proportional limit of PET/RPET sheets in the transverse direction (P<0.001) using Tukey's 95% simultaneous confidence interval.

20% RPET, % RPET>0% RPET>80% RPET, 100% RPET; 0% RPET=60% RPET; 20% RPET, 40% RPET>60% RPET, 80% RPET, 100% RPET; 60% RPET>80% RPET, 100% RPET: 100% RPET<0% RPET, 20% RPET, 40% RPET, 60% RPET 80% RPET, 100% RPET

The properties at the yield point in the transverse direction were determined with the same method as for the machine direction. The yield stress values in the transverse direction did not have the noticeable trend that was found in the machine direction (Table 3). This again may be attributed to the orientation of the crystals in the machine direction causing the mechanical properties of the transverse direction to be more dependent on the amorphous regions. Statistical analysis indicated that the following relationships hold for the yield stress of PET/RPET sheets in the transverse direction (P<0.001) using Tukey's 95% simultaneous confidence interval.

0% RPET=20% RPET, 40% RPET, 100% RPET; 0% RPET<60% RPET, 80% RPET; 20% RPET, 40% RPET, 100% RPET<60% RPET; 60% RPET, 80% RPET>20% RPET; 60% RPET=80% RPET

The strain at yield in the transverse direction followed a similar trend as the strain at the proportional limit in the machine direction. Statistical analysis indicated that the following relationships hold for the yield strain of PET/RPET sheets in the transverse direction (P<0.001) using Tukey's 95% simultaneous confidence interval.

20% RPET>60% RPET, 80% RPET, 100% RPET; 40% RPET=80% RPET; 40% RPET>80% RPET, 100% RPET; 60% RPET=80% RPET; 60% RPET, 80% RPET, 100% RPET<0% RPET<20% RPET, 40% RPET

The Young's Modulus (YM) of PET/RPET sheets was determined for each sheet type for the transverse direction. The YM values decreased steadily with increasing RPET concentrations up to 40% then sharply increased above the 0-40% RPET sheets (Table 3). Statistical analysis indicated that the following relationships hold for the yield strain of PET/RPET sheets in the transverse direction (P<0.001) using Tukey's 95% simultaneous confidence interval.

0% RPET=20% RPET; 0% RPET, 20% RPET<60% RPET, 80% RPET, 100% RPET; 60% RPET=80% RPET=100% RPET

TABLE 3

| Sample | Stress (MPa) @ LOP | Strain @ LOP | Stress (MPa) @ Yield@ | Strain Yield | Young's Modulus (MPa) |
|---|---|---|---|---|---|
| 0% | 47.1 | 0.0475 | 56.1 | 0.0667 | 993 |
| 20% | 50.3 | 0.0516 | 56.6 | 0.0711 | 974 |
| 40% | 49.6 | 0.0541 | 56.1 | 0.0706 | 918 |
| 60% | 49.9 | 0.0475 | 58.0 | 0.0639 | 1050 |
| 80% | 48.0 | 0.0449 | 57.2 | 0.0627 | 1068 |
| 100% | 45.4 | 0.0428 | 56.1 | 0.0629 | 1060 |

Plasma Atomic Emission Spectroscopy

Figure 7:
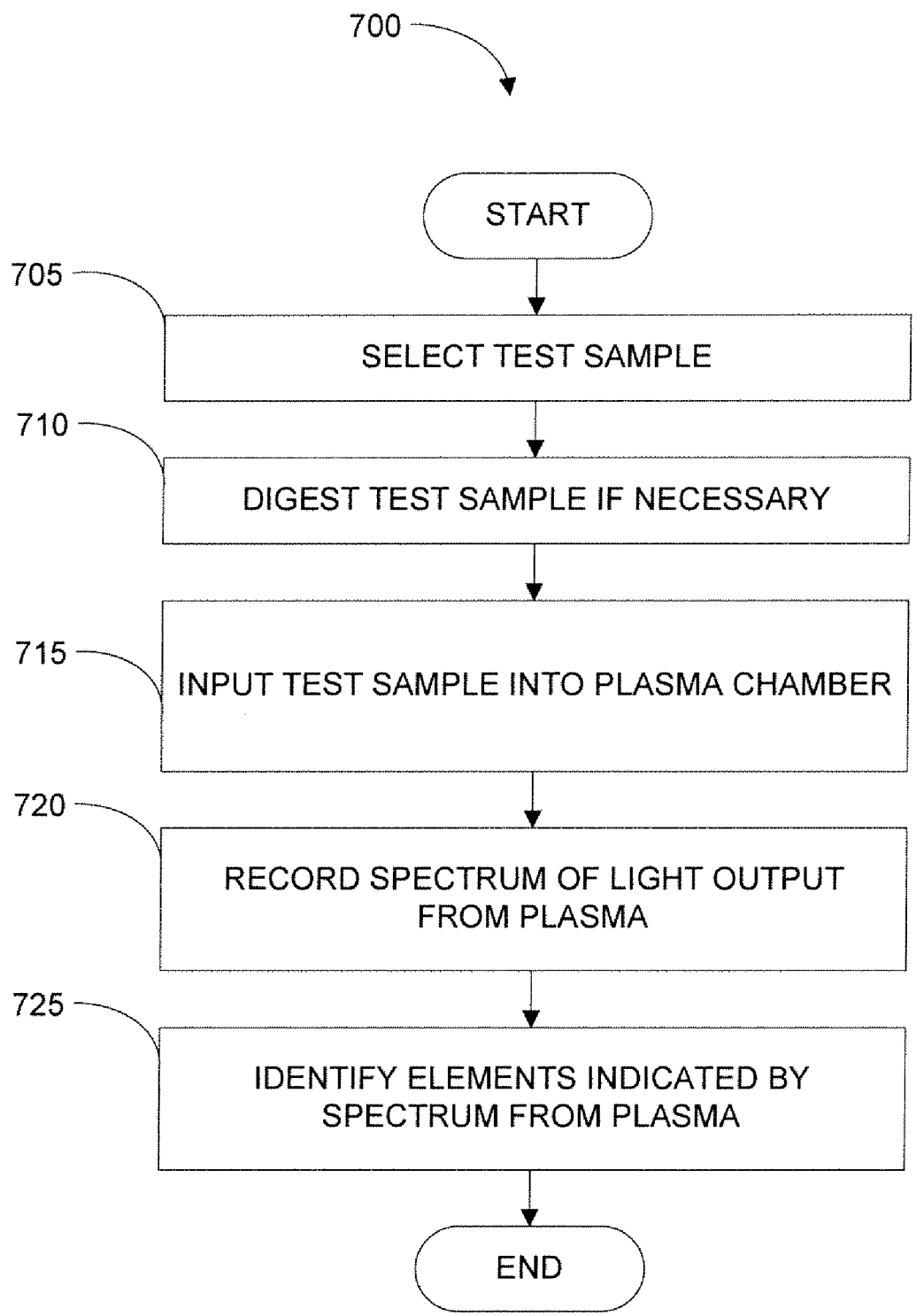
FIG. 7 is a flowchart of the method operations for performing an inductively coupled plasma atomic emission spectroscopy the coated PET sheets, in accordance with embodiments of the described invention.

The coated PET sheets were analyzed by inductively coupled plasma-atomic emission spectroscopy for elemental composition. It should be understood that any type (inductively coupled, RF, capacitively coupled, etc.) of plasma-atomic emission spectroscopy could be used to generate similar analysis results. One or more test samples from each coated sheet were analyzed for elemental composition to ensure that introducing RPET into extruded sheets is safe for food and cosmetic packaging applications. FIG. 7 is a flowchart of the method operations 700 for performing a plasma atomic emission spectroscopy of the coated PET sheets, in accordance with embodiments of the described invention. The operations illustrated herein are by way of example, as it should be understood that some operations may have sub-operations and in other instances, certain operations described herein may not be included in the illustrated operations. With this in mind, the method and operations 700 will now be described.

In an operation 705, a test sample is selected from a selected RPET containing sheet. The test sample can be as large as or as small as may be needed for the specific inductively coupled plasma-atomic emission spectroscopy process.

In an operation 710, the selected test sample is digested into an aqueous or solvent based solution. This is commonly done by treatment with hot mineral acids, oxidation with liquid reagents (e.g. sulfuric acid, nitric acid, and perchloric acid) known as wet ashing, combustion in an oxygen bomb, ashing at high temperature, or high temperature fusion with reagents (e.g. boric oxide, sodium carbonate, sodium peroxide, or potassium pyrosulfate. Operation 710 may be optional for an inductively coupled plasma-atomic emission spectroscopy process capable of analyzing solid samples. Methods such as electrothermal vaporization, laser and spark ablation, and glow discharge vaporization can be beneficial for analyzing solid samples.

In an operation 715, the digested test sample is introduced into the inductively coupled plasma (ICP) chamber. Test samples are typically introduced into the ICP by an inert carrier gas (e.g., nitrogen, argon or other noble gases or any other gas that is inert in the ICP process). The physical condition test samples may therefore be an aerosol, thermally generated vapor, or fine powder or other form suitable as compatible with the ICP.

In an operation 720, the spectrum of light output from the plasma in the ICP is monitored and recorded. Subsequent analysis of the spectrum identifies elemental constituents of the test sample in an operation 725 and the method operations can end.

Data Correction of the with Linear Regression and Logit for Reference Standard Library The data analysis can identify a subset of variables that are independent of the mold release coating and are accurate predictors of % RPET. Test samples were measured using the variables discussed above and as presented in the following Table 4.

TABLE 4

| Variable | Mean | SD | λ-Score | Prob. |
|---|---|---|---|---|
| Hc | 24.49 | 1.40 | 12.754 | 0.000 |
| Tg | 83.26 | 2.18 | 12.467 | 0.000 |
| Hm2 | 30.77 | 3.38 | 11.756 | 0.001 |
| Tcwidth | 13.00 | 2.07 | 7.815 | 0.005 |
| Tm2offset | 254.38 | 1.16 | 6.687 | 0.010 |
| DEGContent | 4.09 | 0.21 | 4.902 | 0.027 |
| Tm2 | 248.50 | 1.18 | 4.902 | 0.027 |
| TgReverse | 74.82 | 1.65 | 3.544 | 0.060 |
| Hm1 | 34.83 | 2.13 | 2.879 | 0.090 |
| Tcoffset | 131.16 | 1.91 | 0.895 | 0.344 |
| Tconset | 227.89 | 3.05 | 0.707 | 0.400 |
| CRYSTAL | 8.99 | 1.71 | 0.496 | 0.481 |
| Tm1 | 251.67 | 1.38 | 0.108 | 0.742 |
| Tc | 137.55 | 2.06 | 0.032 | 0.859 |
| Tm2width | 26.49 | 2.50 | 0.030 | 0.863 |
| ABVm | 1.56 | 0.15 | 0.003 | 0.958 |

A variable subset that is independent of the mold release was scored either 1 or 0 and a binary logistic regression analysis was used. Table 4 includes the means, standard deviations, and the test statistic, λ-Score for each reported variable value. These values reveal if the measurement is influence by the mold release. Higher λ-Score values are confounded by the mold release and lower λ-Score values are un-confounded by the mold release.

A subset of variables that are independent of the mold release can be identified by applying a systematic "search on directed t" using a binary logistic regression. Using this method, variables with small λ-scores were entered into the regression one at a time. After each entry, the Cox-Snell value was calculated. The results are presented in Table 5:

TABLE 5

| Added Variable | $x^2$ | df | Prob. | $R^2$ |
|---|---|---|---|---|
| ABVm | 0.003 | 1 | 0.958 | 0.000 |
| Tm2width | 0.042 | 2 | 0.979 | 0.001 |
| Tm1 | 0.339 | 3 | 0.952 | 0.006 |
| Tm2onset | 13.725 | 4 | 0.008 | 0.204 |

Sequential testing and evaluation reveals that four measurement variables are collectively independent of the mold release coating treatment (i.e., the selected contaminant): tm2width, tc, tm1, and crystal. As reported in Table 5, the independence requirement breakdowns when the fifth variable, tm2Onset, is entered in the binary logistic regression, $x^2=18.3$, df=5, p<0.05, and the Cox-Snell $R^2=0.263$.

The next step in the data analysis sought to identify the best subset linear model for the prediction of % RPET. The modeling reported in Table 6 used ordinary least squares regression analysis to find the best fit. The variables, tm2width, tc, tm1, and crystal, were regressed onto % RPET and the results are presented under the 4 variable model in Table 6.

TABLE 6

| 4 variable model | Parm. | Std. Error | Beta | t-value | Prob. |
|---|---|---|---|---|---|
| (Constant) | −205.201 | 386.539 | | −0.531 | 0.598 |
| % Crystal | 9.787 | 1.568 | 0.486 | 6.243 | 0.000 |
| Tm1 | 4.334 | 1.384 | 0.173 | 3.131 | 0.003 |
| Tc | −7.023 | 1.112 | −0.420 | −6.313 | 0.000 |
| Tm2width | 1.606 | 0.812 | 0.116 | 1.978 | 0.053 |

The slope for tm2Width was not statistically significant at the 0.05 level so it was dropped. The results of the remaining 3-variable, quantitatively different, subset are reported in Table 7. The fit for this model is good, $R^2$=0.937.

TABLE 7

| 3 variable model | Parm. | Std. Error | Beta | t-value | Prob. |
|---|---|---|---|---|---|
| (Constant) | 77.717 | 368.339 | | 0.211 | 0.834 |
| % Crystal | 11.508 | 1.338 | 0.571 | 8.602 | 0.000 |
| Tm1 | 3.025 | 1.247 | 0.121 | 2.426 | 0.019 |
| Tc | −6.488 | 1.107 | −0.388 | −5.862 | 0.000 |

A graph of the % RPET and predicted % RPET is shown in FIG. 2F. FIG. 8 is a graph 800 of a % RPET and a predicted % RPET, in accordance with embodiments of the described invention.

Measuring % RPET via Indicators

This section presents a general method for estimating % RPET. The following indicators of % RPET listed below are used in the measurement model:

Crystallization temperature ($T_c$) (See FIGS. 2A, 2B)
Crystallization peak width ($T_c$ width) (See FIGS. 2A, 2D)
Percent crystallization (% crystallization) (See FIGS. 2A, 2E)
Heat of melting first heat cycle ($\Delta H_m'$) (See FIGS. 2A, 2F)
Absorbance at 350 nm (See FIGS. 4A-4D)

As described above, the above indicators were quantitatively different for the selected contaminant (mold release coating) and the selected thermoplastic (PET) and therefore can reliably identify the percentage of RPET in an unknown virgin PET/RPET sample. It should be understood that other contaminants may require additional or entirely different indicators to identify the ratio (percentage) of RPET in an unknown ratio virgin PET/RPET sample. Further, in other types of thermoplastics additional or entirely different indicators may be used to identify the percentage of recycled thermoplastic in an unknown ratio virgin thermoplastic/recycled thermoplastic sample.

Figure 9:
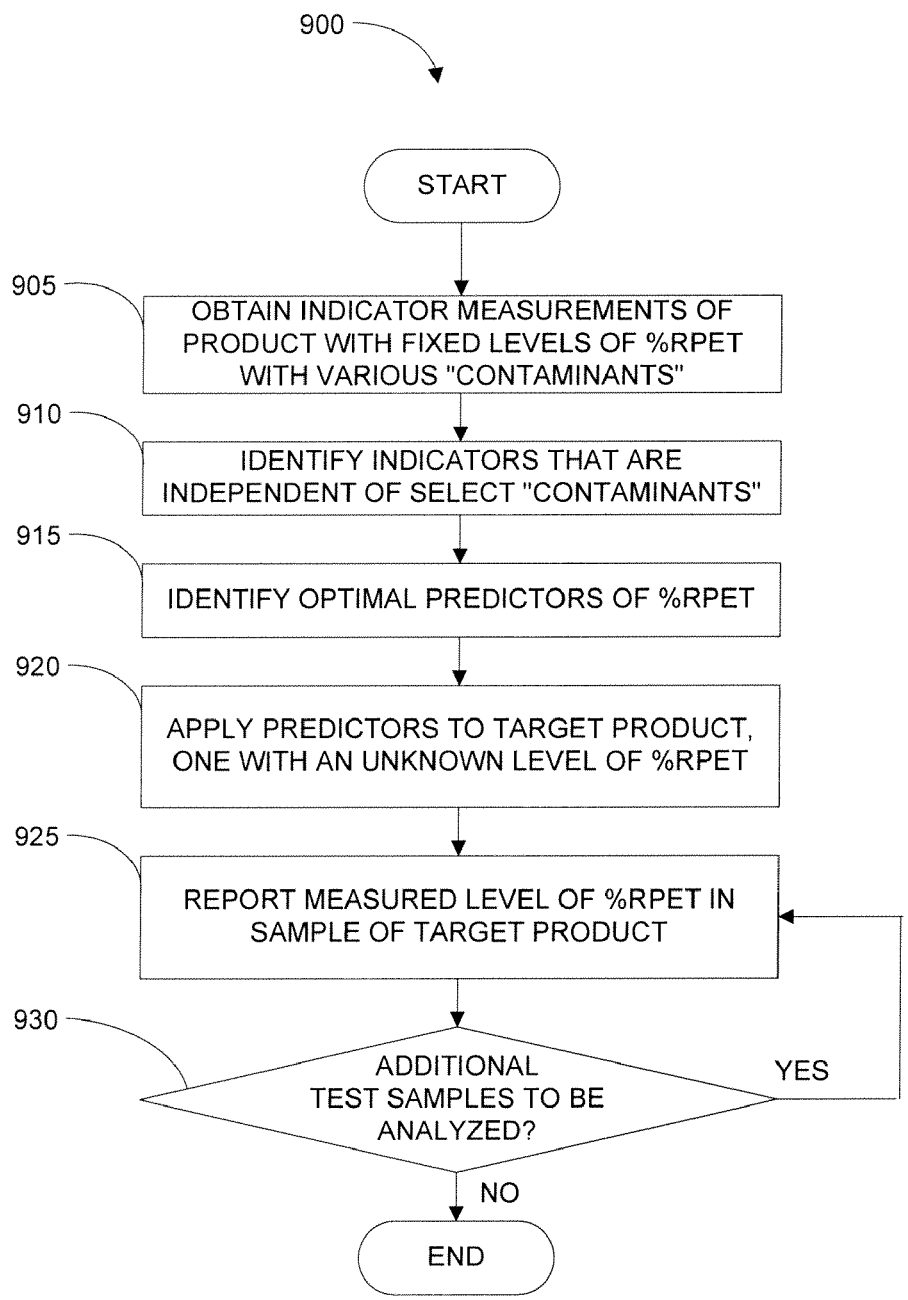
FIG. 9 is a flowchart of the method operations for performing an analysis of an unknown ratio virgin PET/RPET sample, in accordance with embodiments of the described invention.

FIG. 9 is a flowchart of the method operations 900 for performing an analysis of an unknown ratio virgin PET/RPET sample, in accordance with embodiments of the described invention. The operations illustrated herein are by way of example, as it should be understood that some operations may have sub-operations and in other instances, certain operations described herein may not be included in the illustrated operations. With this in mind, the method and operations 900 will now be described.

In an operation 905, determine models of known ratio virgin PET/RPET along with various contaminants as are commonly found in RPET as described in more detail in the preceding descriptions of FIGS. 1-8.

In an operation 910, indicators that are statistically independent of a selected contaminant are identified. By way of example, the selected contaminant is the mold release coating. Indicators that are statistically independent of a selected contaminant are identified as described above regarding data correction of with linear regression and logit. This operation applies tools such as binary logit analysis and filters out indicators that show bias due the selected contaminant.

In an operation 915, the results of operation 910 identify indicators that are statistically independent of the selected contaminant and the list of indicators is reduced to an optimal subset of statistically independent indicators. Generalized linear modeling is a flexible generalization of ordinary least squares regression. Generalized linear modeling allows for the various distributions (Binomial, Poisson, Gaussian) for the measurement model to be related to the percentage of RPET via a link function (e.g. logit, probit, etc.), and allows the magnitude of the variance of each measurement to be a function of its predicted value.

In an operation 920, the optimal subset of indicators are used to estimate the percentage of RPET in the test sample. Multiple test samples from a single test material may be required to accurately provide the required results. The test samples are extracted from a test material having an unknown ratio of virgin PET/RPET. The test samples can be prepared as described in FIG. 10 below.

In an operation 925, the test samples are analyzed using the analytical procedures necessary to identify the data points for each of the optimal subset of indicators. These data points are recorded.

In an operation 930, if there are more test samples to analyze then the method operations continue in operation 925. If there are no more test samples to be analyzed, then the method operations can end.

Preparation of Unknown Ratio Test Samples

Figure 10:
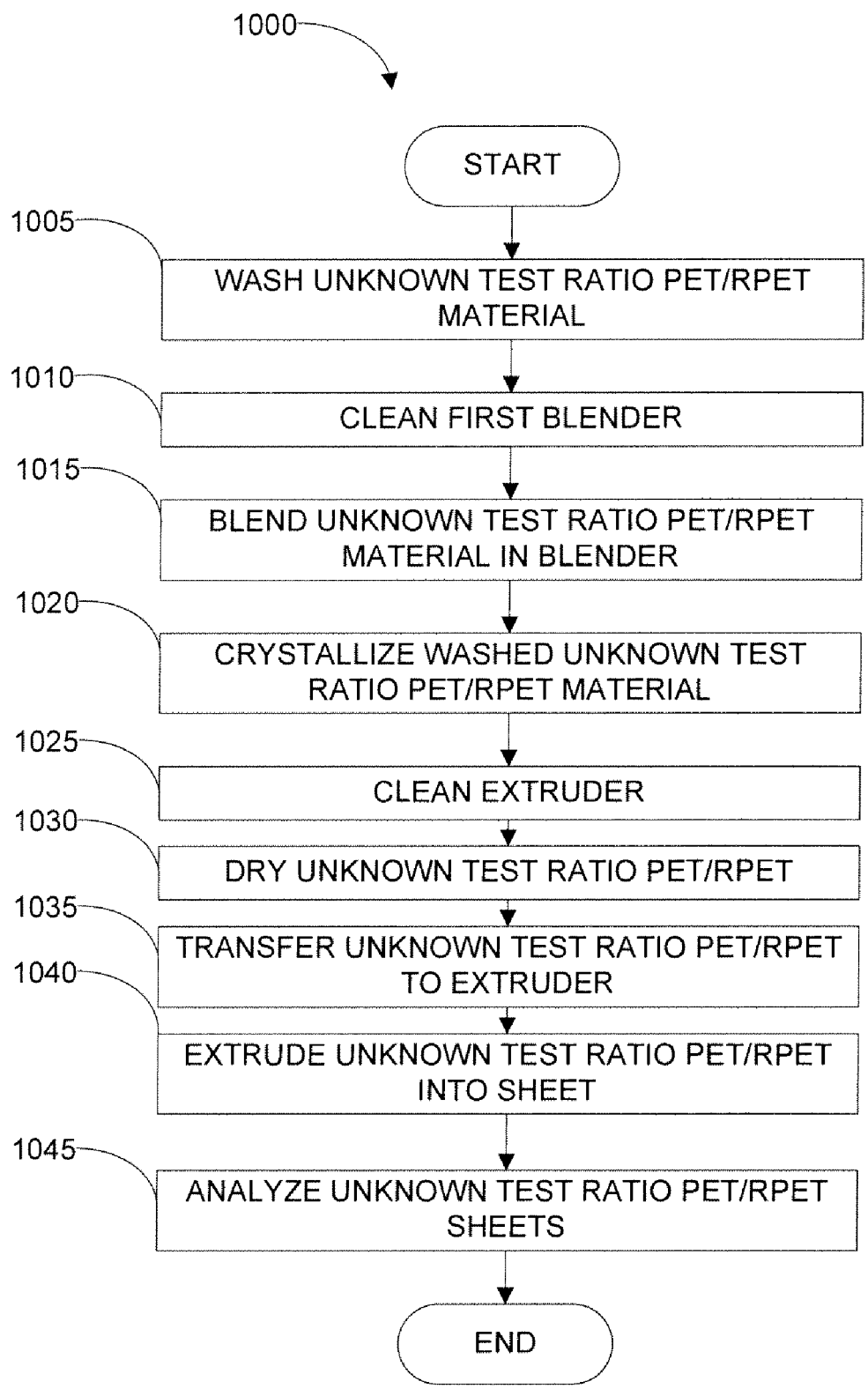
FIG. 10 is a flowchart of the method operations for producing the unknown ratio virgin PET/RPET test samples, in accordance with embodiments of the described invention.

The unknown ratio test samples can be formed in test samples similar to the control samples described above. FIG. 10 is a flowchart of the method operations 1000 for producing the unknown ratio virgin PET/RPET test samples, in accordance with embodiments of the described invention. The operations illustrated herein are by way of example, as it should be understood that some operations may have sub-operations and in other instances, certain operations described herein may not be included in the illustrated operations. With this in mind, the method and operations 1000 will now be described.

In an operation 1005, a quantity of the unknown test ratio PET/RPET is washed to remove undesirable contaminants. Washing can include multiple sub steps such as washing with solvents, detergents, rinse agents and drying as are well known in the art.

In an optional, as may be required, operation 1010, a first blender is cleaned by cleaning with a suitable cleaning process or by purging if necessary. The first blender is purged to substantially remove any contaminants in the first blender.

In an optional operation 1015, the washed unknown ratio PET/RPET is transferred to the first blender and blended therein to a substantially uniform size flake. A typical PET flake size is between about 0.4 and about 8 mm in diameter.

In another optional operation 1020, the washed, blended unknown ratio PET/RPET is transferred from the first blender to a crystallizer The washed, blended unknown ratio PET/RPET is crystallized in the crystallizer to substantially crystallize (e.g., align) the polymer chains in the washed, blended unknown ratio PET/RPET material to provide a substantially homogeneous density of the washed, blended unknown ratio PET/RPET.

In an operation 1025, the extruder is purged as described in more detail above. In an operation 1030, the washed, blended, crystallized, unknown ratio PET/RPET is transferred to a drier. The washed, blended, crystallized, unknown ratio PET/RPET can be dried to achieve a desired moisture content as described above.

In an operation 1035, the washed, blended, crystallized, dried, unknown ratio PET/RPET is transferred to an extruder. In an operation 1040, the extruder produces unknown ratio PET/RPET sheets having a selected thickness (e.g., from less than about 5 mil to about 500 mil or more) substantially similar to the control sample sheets described above.

In an operation 1045, the unknown ratio PET/RPET sheets are analyzed substantially similar to the control sample analysis described in more detail above. The analysis can include one or more of differential scanning calorimetry, ultraviolet-visible (UV-Vis) spectroscopy, physical thickness, attenuated total reflectance Fourier transform infrared spectroscopy (ATR-FTIR) and mechanical analysis.

With the above embodiments in mind, it should be understood that the invention may employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations described herein that form part of the invention are useful machine operations. The invention also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data maybe processed by other computers on the network, e.g., a cloud of computing resources.

The embodiments of the present invention can also be defined as a machine that transforms data from one state to another state. The transformed data can be saved to storage and then manipulated by a processor. The processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine.

The invention can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, DVDs, Flash, magnetic tapes, and other optical and non-optical data storage devices. The computer readable medium can also be distributed over a network coupled computer systems so that the computer readable code is stored and executed in a distributed fashion.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. Method of identifying a reference standard library for thermoplastic content comprising:
    preparing a plurality of samples of each one of a plurality of known ratios of virgin thermoplastic/recycled thermoplastic;
    analyzing each of the plurality of samples of each one of the plurality of known ratios of virgin thermoplastic/recycled thermoplastic with at least one of a group of analyses consisting of:
        a differential scanning calorimetry analysis;
        a physical thickness analysis;
        an ultraviolet-visible spectroscopy analysis;
        an attenuated total reflectance Fourier transform infrared spectroscopy analysis;
        a mechanical analysis; or
        a plasma atomic emission spectroscopic analysis;
    selecting a contaminant;
    identifying a first plurality of indicators output from the at least one of the group of analyses;
    identifying a second plurality of indicators from the first plurality of indicators, the second plurality of indicators being independent of the selected contaminant; and
    optimizing the second plurality of indicators to identify a third plurality of indicators, the third plurality of indicators being quantitatively different of the selected contaminant wherein each one of the third plurality of indicators has at least one corresponding value for each one of the plurality of known ratios of virgin thermoplastic/recycled thermoplastic.

2. The method of claim 1, wherein the thermoplastic is a polyethylene terephthalate (PET).

3. The method of claim 1, wherein the thermoplastic is one of a plurality of thermoplastics consisting of: a polyethylene, a polypropylene, a polystyrene, a poly methyl methacrylate, a polycarbonate, an addition polymer or a condensation polymer.

4. The method of claim 1, wherein analyzing each of the plurality of samples of each one of the plurality of known ratios of virgin thermoplastic/recycled thermoplastic includes analyzing each of the plurality of samples of each one of the plurality of known ratios of virgin thermoplastic/recycled thermoplastic with at least two of the group of analyses.

5. A method for determining content of recycled thermoplastic in a thermoplastic sample comprising:
    identifying a reference standard library for thermoplastic content including a plurality of indicators being quantitatively different of the selected contaminant;
    preparing a plurality of test samples of an unknown ratio of virgin thermoplastic/recycled thermoplastic for analysis;
    analyzing each one of the plurality of test samples of the unknown ratio of virgin thermoplastic/recycled thermoplastic with at least one of a group of analyses consisting of:
        a differential scanning calorimetry analysis;
        a physical thickness analysis;
        an ultraviolet-visible spectroscopy analysis;
        an attenuated total reflectance Fourier transform infrared spectroscopy analysis;
        a mechanical analysis; or
        a plasma atomic emission spectroscopic analysis;
    wherein analyzing each one of the plurality of test samples of the unknown ratio of virgin thermoplastic/recycled thermoplastic includes identifying a corresponding value for each one of the plurality of indicators quantitatively different of the selected contaminant for the unknown ratio of virgin thermoplastic/recycled thermoplastic; and identifying a percentage of virgin thermoplastic and recycled thermoplastic includes comparing the corresponding value for each one of the plurality of indicators quantitatively different of the selected contaminant for the unknown ratio of virgin thermoplastic/recycled thermoplastic to the reference standard library.

6. The method of claim 5, wherein analyzing each one of the plurality of test samples of the unknown ratio of virgin thermoplastic/recycled thermoplastic with at least one of a group of analyses includes analyzing each one of the plurality of test samples of the unknown ratio of virgin thermoplastic/recycled thermoplastic with at least two of the group of analyses.

7. The method of claim 5, the thermoplastic is a polyethylene terephthalate (PET).

8. The method of claim 5, wherein the thermoplastic is one of a plurality of thermoplastics consisting of: a polyethylene, a polypropylene, a polystyrene, a poly methyl methacrylate, a polycarbonate, an addition polymer or a condensation polymer.

9. A testing system for identifying a reference standard library for thermoplastic content comprising:
   a system for preparing a plurality of samples of each one of a plurality of known ratios of virgin thermoplastic/recycled thermoplastic;
   an analysis system for analyzing each of the plurality of samples of each one of the plurality of known ratios of virgin thermoplastic/recycled thermoplastic with at least one of a group of analyses consisting of:
      a differential scanning calorimetry analysis;
      a physical thickness analysis;
      an ultraviolet-visible spectroscopy analysis;
      an attenuated total reflectance Fourier transform infrared spectroscopy analysis;
      a mechanical analysis; or
      a plasma atomic emission spectroscopic analysis;
   selecting a contaminant;
   a first identifier for identifying a first plurality of indicators output from the at least one of the group of analyses;
   a second identifier for identifying a second plurality of indicators from the first plurality of indicators, the second plurality of indicators being independent of the selected contaminant; and
   an optimizer for optimizing the second plurality of indicators to identify a third plurality of indicators, the third plurality of indicators being quantitatively different of the selected contaminant wherein each one of the third plurality of indicators has at least one corresponding value for each one of the plurality of known ratios of virgin thermoplastic/recycled thermoplastic.

10. A testing system for determining content of recycled thermoplastic in a thermoplastic sample comprising:
   an identifier for identifying a reference standard library for thermoplastic content including a plurality of indicators being quantitatively different of the selected contaminant;
   a system for preparing a plurality of test samples of an unknown ratio of virgin thermoplastic/recycled thermoplastic for analysis;
   an analyzer for analyzing each one of the plurality of test samples of the unknown ratio of virgin thermoplastic/recycled thermoplastic with at least one of a group of analyses consisting of:
      a differential scanning calorimetry analysis;
      a physical thickness analysis;
      an ultraviolet-visible spectroscopy analysis;
      an attenuated total reflectance Fourier transform infrared spectroscopy analysis;
      a mechanical analysis; or
      a plasma atomic emission spectroscopic analysis;
   wherein analyzing each one of the plurality of test samples of the unknown ratio of virgin thermoplastic/recycled thermoplastic includes identifying a corresponding value for each one of the plurality of indicators quantitatively different of the selected contaminant for the unknown ratio of virgin thermoplastic/recycled thermoplastic; and
   an identifier for identifying a percentage of virgin thermoplastic and recycled thermoplastic includes comparing the corresponding value for each one of the plurality of indicators quantitatively different of the selected contaminant for the unknown ratio of virgin thermoplastic/recycled thermoplastic to the reference standard library.

* * * * *